(12) United States Patent
Horne

(10) Patent No.: US 10,736,577 B2
(45) Date of Patent: Aug. 11, 2020

(54) METHOD AND SYSTEM FOR ASSESSING MOTION SYMPTOMS

(71) Applicant: Global Kinetics Pty Ltd, Melbourne (AU)

(72) Inventor: Malcolm Kenneth Horne, Melbourne (AU)

(73) Assignee: GLOBAL KINETICS PTY LTD, Melbourne (AU)

( * ) Notice: Subject to any disclaimer, the term of this patent is extended or adjusted under 35 U.S.C. 154(b) by 153 days.

(21) Appl. No.: 15/123,568

(22) PCT Filed: Mar. 3, 2015

(86) PCT No.: PCT/AU2015/050084
§ 371 (c)(1),
(2) Date: Sep. 2, 2016

(87) PCT Pub. No.: WO2015/131244
PCT Pub. Date: Sep. 11, 2015

(65) Prior Publication Data
US 2017/0079597 A1    Mar. 23, 2017

(30) Foreign Application Priority Data

Mar. 3, 2014 (AU) ................................ 2014900683
Sep. 17, 2014 (AU) ................................ 2014903705

(51) Int. Cl.
| A61B 5/11 | (2006.01) |
| A61B 5/00 | (2006.01) |
| G16H 20/30 | (2018.01) |
| A61B 5/16 | (2006.01) |
| G16H 50/30 | (2018.01) |

(52) U.S. Cl.
CPC .......... *A61B 5/7275* (2013.01); *A61B 5/1101* (2013.01); *A61B 5/16* (2013.01);
(Continued)

(58) Field of Classification Search
CPC ........ A61B 5/11; A61B 5/1101; A61B 5/4082
See application file for complete search history.

(56) References Cited

U.S. PATENT DOCUMENTS

| 4,306,291 A | 12/1981 | Zilm et al. |
| 4,730,253 A | 3/1988 | Gordon |
(Continued)

FOREIGN PATENT DOCUMENTS

| EP | 0535508 A1 | 4/1993 |
| EP | 1595497 A1 | 11/2005 |
(Continued)

OTHER PUBLICATIONS

Perlmutter, Joel S., and Jonathan W. Mink. "Deep Brain Stimulation." Annual Review of Neuroscience, vol. 29, No. 1, 2006, pp. 229-257., doi:10.1146/annurev.neuro.29.051605.112824.*
(Continued)

*Primary Examiner* — Sean P Dougherty
*Assistant Examiner* — David Joseph Fernandez-Fidalgo
(74) *Attorney, Agent, or Firm* — Neal, Gerber & Eisenberg LLP

(57) ABSTRACT

A state of progression in an individual of a disease or treatment having motion symptoms is determined. A time series of accelerometer data is obtained from an accelerometer worn on an extremity of the person, over an extended period during everyday activities of the person. The accelerometer data is processed to produce a plurality of measures of kinetic state of the individual at a respective plurality of times throughout the extended period, each measure of kinetic state comprising at least one of: a measure for bradykinesia, and a measure for dyskinesia. A measure of dispersion of the measures of kinetic state is determined. An output is generated, indicating that motion symptoms are at an initial stage if the measure of dispersion is less than a threshold, or indicating that motion symptoms are at an advanced stage if the measure of dispersion is greater than the threshold.

10 Claims, 12 Drawing Sheets

(52) U.S. Cl.
CPC .......... *A61B 5/4076* (2013.01); *A61B 5/4082* (2013.01); *A61B 5/4842* (2013.01); *G16H 20/30* (2018.01); *G16H 50/30* (2018.01)

(56) References Cited

U.S. PATENT DOCUMENTS

| | | | |
|---|---|---|---|
| 4,771,792 | A | 9/1988 | Seale |
| 4,817,628 | A | 4/1989 | Zealear et al. |
| 4,836,218 | A | 6/1989 | Gay et al. |
| 5,293,879 | A | 3/1994 | Vonk et al. |
| 5,913,310 | A | 6/1999 | Brown |
| 6,053,866 | A | 4/2000 | McLeod |
| 6,561,992 | B1 | 5/2003 | Eberhart et al. |
| 6,878,121 | B2 | 4/2005 | Krausman et al. |
| 7,983,872 | B2 | 7/2011 | Makino et al. |
| 8,187,209 | B1 | 5/2012 | Giuffrida |
| 10,085,689 | B1 | 10/2018 | Giuffrida et al. |
| 2002/0082222 | A1 | 6/2002 | Shapira et al. |
| 2002/0156392 | A1 | 10/2002 | Arai et al. |
| 2004/0087878 | A1 | 5/2004 | Krausman et al. |
| 2004/0220493 | A1 | 11/2004 | Teicher et al. |
| 2005/0075553 | A1 | 4/2005 | Sakai et al. |
| 2005/0234309 | A1* | 10/2005 | Klapper ............... A61B 5/1101 600/300 |
| 2005/0240086 | A1 | 10/2005 | Akay |
| 2005/0283096 | A1* | 12/2005 | Chau ................... A61B 5/11 600/593 |
| 2006/0287614 | A1 | 12/2006 | Hogan et al. |
| 2008/0033259 | A1 | 2/2008 | Manto et al. |
| 2008/0045804 | A1 | 2/2008 | Williams |
| 2008/0053253 | A1 | 3/2008 | Moore et al. |
| 2009/0062696 | A1 | 3/2009 | Nathan et al. |
| 2009/0326419 | A1 | 12/2009 | Gonzalez Rojas et al. |
| 2010/0030119 | A1 | 2/2010 | McNames et al. |
| 2011/0098608 | A1 | 4/2011 | Griffiths et al. |
| 2014/0074179 | A1 | 3/2014 | Heldman et al. |
| 2014/0364770 | A1 | 12/2014 | Slonneger et al. |
| 2015/0073310 | A1 | 3/2015 | Pracar et al. |
| 2015/0157274 | A1 | 6/2015 | Ghassemzadeh et al. |

FOREIGN PATENT DOCUMENTS

| | | |
|---|---|---|
| EP | 1714612 A2 | 10/2006 |
| EP | 1994883 A1 | 11/2008 |
| EP | 2660745 A2 | 11/2013 |
| JP | 2004136074 A | 5/2004 |
| JP | 2004261525 A | 9/2004 |
| JP | 2005152053 A | 6/2005 |
| JP | 2007075428 A | 3/2007 |
| WO | 1997039677 A1 | 10/1997 |
| WO | 1999052038 A1 | 10/1999 |
| WO | 2003053245 A2 | 7/2003 |
| WO | 03063876 A2 | 8/2003 |
| WO | 2004008427 A1 | 1/2004 |
| WO | 2004084725 A1 | 10/2004 |
| WO | 2005120347 A1 | 12/2005 |
| WO | 2006088415 A1 | 8/2006 |
| WO | 2006105621 A1 | 10/2006 |
| WO | 2007105648 A1 | 9/2007 |
| WO | 2007136677 A2 | 11/2007 |
| WO | 2008037260 A2 | 4/2008 |
| WO | 2009149520 A1 | 12/2009 |
| WO | 2012129636 A1 | 10/2012 |
| WO | 2013012625 A1 | 1/2013 |
| WO | 2014131090 A1 | 9/2014 |
| WO | 2015118534 A1 | 8/2015 |
| WO | 2015131244 A1 | 9/2015 |

OTHER PUBLICATIONS

Aug. 1, 2013—(US) Maglione et al., Actigraphy for the Assessment of Sleep Measures in Parkinson's Disease, pp. 1209-1217, https://doi.org/10.5665/sleep.2888.
Aug. 19, 2014—(US) Pan et al., Quantitative Evaluation of the Use of Actigraphy for Neurological and Psychiatric Disorders Behaviioural Neurology, vol. 2014, http://dx.doi.org/10.1155/2014/897282.
2016 vol. 53, No. 4 (US) Bhidayasiri et al., Capturing Nighttime Symptoms in Parkinson Disease: Technical Development and Experimental Verification of Inertial Sensors for Nocturnal Hypokinesia, http://dx.doi.org/10.1682/JRRD.2015.04.0062.
Apr. 21, 2017—(AU) Search Report—App. No. 2016902203.
Aug. 9, 2017—(WO) International Search Report and Written Opinion—App. No. PCT/AU2017/050555.
Mar. 31, 2017—(EP) International Search Report—App. No. PCT/AU2017/050015.
Nov. 25, 2013—(AU) Search Report (International-type)—App. 2013903014.
Sep. 1, 2015—(WO) International Preliminary Report on Patentability—App. PCT/AU2014/000191.
Jun. 30, 2017—(AU) Examination Report—App. 2014223313.
Aug. 9, 2018—(IN) Examination Report—App. 211/CHENP/2011.
Kimura, Y., "Quantitative Observation of a Tremor using an Accelerometer", Dokkyo Journal of Medical Scioences, 1996.
May 5, 2015—(PCT) International Search Report—App. PCT/AU2015/050084.
Sep. 16, 2016 (EP) Extended European Search Report—App. 14756592.3.
Mar. 27, 2014 (PCT)—International Search Report and Written Opinion—App. PCT/AU2014/000191.
Motor Inhibition and Cognitive Flexibility in Obssessive-Compulsive Disorder and Trichotillomania, Samuel R. Chamberlain, M.A., et al., Am. J. Psychiatry, Jul. 2006:163: pp. 1282-1284.
Impulse inhibition in people with Internet addiction disorder; Electrophysiological evidence from a Go/No Go study, Guangheng Dong, et al., Nueoscience Letters 485, © 2010 Elsevier Ireland Ltd., pp. 138-142.
Cognitive dysfunction in childhood-onset pathologic skin picking, Jon E. Grant, et al., Journal of Obsessive-Compulsive and Related Disorders, © 2012 Elsevier Ltd., pp. 73-76.
Automatic Assessment of Levodopa-Induced Dyskinesias in Daily Life by Neural Networks, Noël L.W. Kleijsers, MSc, et al., Movement Disorders, vol. 18, No. 1, 2003, © 2002 Movement Disorder Society, pp. 70-80.
Defining Parkinson's Disease and Parkinsonism, Rajesh Pahwa et al, Etiology of Parkinson's Disease, 1995, pp. 1-54.
The Relation Between EMG Activity and Kinematic Parameters Strongly Supports a Role of the Action Tremor in Parkinsonian Bradykinesia, Carboncini, et al., Movement Disorders vol. 16, No. 1, © 2001 Movement Disorder Society, pp. 47-57.
Movement Disorder Society-Sponsored Revision of the Unified Parkinson's Disease Rating Scale (MDS-UPDRS): Scale Presentation and Clinimetric Testing Results, Goetz et al, Movement Disorders vol. 23, No. 15, © 2008 Movement Disorder Society, pp. 2129-2170.
Utility of an Objective Dyskinesia Rating Scale for Parkinson's Disease: Inter- and Intrarater Reliability Asessment, Goetz et al, Movement Disorders vol. 9, No. 4, ©1994 Movement Disorder Society, pp. 390-394.
Accuracy of clinical diagnosis of idiopathic Parkinson's disease: a clinico-pathological study of 100 cases, Hughes et al., Journal of Neurology, Neurosurgery, and Psychiatry 1992 55: pp. 181-184.
A new approach in the assessment of motor activity in Parkinson's disease, van Hilten et al., Journal of Neurology, Neurosurgery, and Psychiatry 1991; 54, pp. 976-979.
Ambulatory accelerometry in Parkinson's disease, Hoff, University of Leiden (Doctoral Thesis), Sep. 30, 2005, 107 pages.
Unified Parkinson's Disease Rating Scale Motor Examination: Are Ratings of Nurses, Residents in Neurology, and Movement Disorders Specialists Interchangeable?, Post et al., Movement Disorders Fol. 20, No. 12, © 2005 Movement Disorder Society, pp. 157-1584.
On the Structure of Motor Symptoms of Parkinson's Disease, Stochl, et al., Movement Disorders vol. 23, No. 9, 2008, pp. 1307-1315.
Online Monitoring of Dyskinesia in Patients with Parkinson's Disease; Utilizing Wearable Movement Sensors to Successfully Detect and Assess Severity of Parkinsonian Symptoms in Daily Life, Keijsers et al., IEEE Engineering in Medical and Biology Magazine, May/Jun. 2003, pp. 96-103.

(56) References Cited

OTHER PUBLICATIONS

Tremorwatch®, Ref RC/SB Issue date Mar. 30, 2007 © Cambridge Neurotechnology 2007, 2 pages.
Kinesia Movement Disorders Assessment System, Wireless Gyroscope, Wireless Accelerometer, http://www.clevemed.com/Kinesia/hardware.shtml, retrieved Aug. 4, 2011, 2 pages.
Shimmer—Sensing Health with Intelligence, Modularity, Mobility, and Experimental Reusability, SHIMMER Hardware Guide Rev. 1.3, dated Oct. 3, 2006 © 2006 Intel Corporation, 15 pages.
Application EMGs spectral analysis method for the objective diagnosis of different clinical forms of Parkinson's disease, Andreeva, et al., Electromyogr.clin.Neurophysiol., 1996, vol. 36, pp. 187-192.
The measurement of tremor using simple laser systems, Beuter, et al., Journal of Neuroscience Methods vol. 53 © 1994 Elsevier Science B.V., pp. 47-54.
Induction of Chorea and Dystonia in Parkinsonian Primates, Boyce et al., Movement Disorders vol. 5, No. 1, © 1990 Movement Disorder Society, pp. 3-7.
A quantitative study of levodopa-induced dyskinesia in Parkinson's disease, Caligiuri et al., Journal of Neural Transmission [P-D Sect] 1993, vol. 6, © Springer-Verlag 1993, pp. 89-98.
Instrumental Assessment of Lingual Motor Instability in Tardive Dyskisia, Caligiuri, et al., Neuropsychopharmacology, vol. 2, No. 4, 1989, pp. 309-312.
Assessment of Rest Tremor in Parkinson's Disease, Cleeves, et al, Advances in Neurology, vol. 45, Raven Press, New York © 1985, pp. 349-352.
Computational Analysisof Open Loop Handwriting Movements in Parkinson's Disease: A Rapid Method to Detect Dopamimetic Effects, Eichhorn, et al., Movement Disorders vol. 11, No. 3, 1996, pp. 289-297.
Gravitational artifact in accelerometric measurements of tremor, Elble, Clinical Neurophysiology, vol. 116, © 2005 Internation Federation of Clinical Neurophysiology, pp. 1638-1643.
Relationship between Tardive Dyskinesia, L-Dopa-Induced Hyperkinesia and Parkinsonism, Gerlach, Psychopharmacology vol. 51, © Springer-Verlag 1977, pp. 259-263.
Quantification of tremor with a digitizing tablet, Elble, et al., Journal of Neuroscience Methods, vol. 32, © 1990 Elsevier Science Publishers B.V., pp. 193-198.
Portable System for Quantifying Motor Abnormalities in Parkinson's Disease, Ghika, et al., ISEE Transactions on Biomedical Engineering, vol. 40, No. 3, © 1993 IEEE, pp. 276-283.
Clinical Neurophysiological Assessment of Parkinson's Disease, Gonce et al., Advances in Neurology, vol. 40, © 1984 Raven Press, New York, pp. 365-373.
Postural and Resting Tremors in Parkinson's Disease, Gresty, et al., Advances in Neurology, vol. 40, © 1984 Raven Press, New York, pp. 361-364.
Spectral analysis of tremor: understanding the results, Gresty, et al., Journal of Neurology, Neurosurgery, and Psychiatry, vol. 53, 1990, pp. 976-981.
Is Parkinsonian Arm Tremor a Resting Tremor?, Hadar, et al., Eur Neurol 1993, vol. 33, pp. 221-228.
Motor response to levodopa in patients with parkinsonian motor fluctuations: a follow-up study over three years, Hughes, et al., Journal of Neurology, Neurosurgery, and Psychiatry, vol. 57, 1994, pp. 430-434.
Disability profiles and objective quantitative assessment in Parkinson's disease, Johnels et al., Acta Neurol. Scand., vol. 79, 1989, pp. 227-238.
Assessment of symptoms of Parkinson's disease by appartive methods, Kraus. et al., J. Neural Transm (1987) [Suppl] vol. 25: pp. 89-96.
Wearable Wireless Sensor Network to Assess Clinical Status in Patients with Neurological Disorders, Lorincz, et al., IPSN '07, Apr. 25-27, 2007, pp. 563-564.
An ambulatory dyskinesia monitor, Manson et al., J. Neurol. Neurosurg. Psychiatry, vol. 68, 2000, pp. 196-201.
Characteristics of Handwriting of Patients with Huntington's Disease, Phillips, et al., Movement Disorders vol. 9, No. 5, 1994, pp. 521-530.
Assessment of Extrapyramidal Disorders, Marsden et al., Br. J. clin.Pharmac, vol. 11, © Macmillan Publishers Ltd. 1981, pp. 129-151.
Levodopa-induced dyskinesia: Review, observations, and speculations, Nutt, Neurology, 1990, vol. 40, pp. 340-345.
Levodopa-Induced Dyskinesias in Parkinson's Disease Phenomenology and Pathophysiology, Marconi, et al., Movement Disorders, vol. 9, No. 1, 1994, pp. 2-12.
Long-term monitoring of gait in Parkinson's disease, Moore, et al., Gait & Posture vol. 26, 2007, pp. 200-207.
Motor complications associated with chronic levodopa therapy in Parkinson's disease, Obeso,et al., Neurology vol. 38, Suppl 2, Nov. 1989, pp. 11-19.
Motor Response to Levodopa and the Evolution of Motor Fluctuations in the First Decade of Treatment of Parkinson's Disease, McColl, et al., Movement Disorders vol. 17, No. 6, © 2002 Movement Disorder Society, pp. 1227-1234.
Short- and Long-Duration Responses to Levodopa During the First Year of Levodopa Therapy, Nutt et all, Annals of Neurology vol. 42, No. 3, Sep. 1997, © 1997 by the Ameircan Neurological Association, pp. 349-355.
Slowness of Movement in Parkinson's Disease, Marsden, Movement Disorders, vol. 1. Suppl. 1, © 1989 Movement Disorder Society, pp. S26-S37.
Observations on the design and specification of a wrist-worn human activity monitoring system, Redmond, et al., Behavior Research Methods, Instruments, and Computers, 1985, vol. 17, No. 6, pp. 659-669.
An Ambulatory System to Quanitfy Bradykinesia and Tremor in Parkinson's Disease, Salarian, et al., Proc. of the 4th Annual IEEE Conf on Information Technology Applications in Biomedicine, UK, © 2003 IEEE, pp. 35-38.
A comparison of neuropsychological effects of thalamotomy and thalamic stimulation, Schuurman, et al., Neurology © 2002, vol. 59, pp. 1232-1239.
Movement Variability and Bradykinesia in Parkinson's Disease, Sheridan, et al., Brain 1990, vol. 113, © Oxford University Press 1990, pp. 1149-1161.
Advanced Analysis of Wearable Sensor Data to Adjust Medication Intake in Patients with Parkinson's Disease, Sherrill, et al., Proceedings of the 2nd International IEEE EMBS Conference on Neural Engineering, Mar. 2005, © 2005 IEEE, pp. v-viii.
Ambulatory monitoring of tremor and other movements before and aftger thalamotomy: a new quantitative technique, van Someren, et al., Journal of the Neurological Sciences, vol. 117, © 1993 Elsevier Science Publishers, pp. 16-23.
A New Actigraph for Long-Term Registration of the Duration and Intesity of Tremor ande Movement, van Someren, et al., IEEE Transactions on Biomedical Engineering, vol. 45, No. 3, Mar. 1998, pp. 386-395.
Actigraphic Monitoring of Movement and Rest-Activity Rhythms in Aging, Alzheimer's Disease, and Parkinson's Disease, Van Someren, IEEE Transactions on Rehabilitation Engineering, vol. 5, No. 4, Dec. 1997, pp. 394-398.
New Actigraph for Long-Term Tremor Recording, Van Someren et al., Movement Disorders, vol. 21, No. 8, 2006, pp. 1136-1143.
Validity of Long-Term Electromyography in the Quanitfication of Tremor, Spieker, et al., Movement Disorders, vol. 12., No. 6, © 1997 Movement Disorders Society, pp. 985-991.
Accelerometric Assessment of Tardive Dyskinesia, Tryon, et al., Am. J. Psychiatry, 1987, vol. 14, No. 12, pp. 1584-1587.
Quantitative Assessment of Parkinsonian Patients by Continuous Wrist Activity Monitoring, Van Hilten, et al., Clinical Neuropharmacology, vol. 16, No. 1, © 1993 Raven Presss, Ltd., pp. 36-45.
Bradykinesia and hypokenisia in Parkinson's disease: what's in a name?, van Hilten, et al., J. Neural Transm, vol. 105, © Springer-Verlag 1998, pp. 229-237.

(56) References Cited

OTHER PUBLICATIONS

Towards a New Method for Kinematic Quantification of Bradykinesia in Patients With Parkinson's Disease Using Triaxial Accelometry, Veltink, et al., 1995 IEEE-EMBC and CMBEC, Theme 5: Neuromuscular Systems/Biomechanics, © IEEE, pp. 1303-1304.
A Normative Study of Postural Tremor of the Hand, Wade et al., Arch. Neurol., vol. 39, Jun. 1982, pp. 358-362.
Quantification of Chorea in Huntington's Disease by Power Spectral Analysis, Weitzman, et al., Diseases of the Nervous System, May 1976, pp. 264-268.
Bradykinesia in Parkinson's Disease: Disorders of Onset and Execution of Fast Movement, Yanagisawa, et al., Eur Neurol 1989, vol. 29, Suppl. 1, © 1989 S. Karger AG, pp. 19-28.
Pathophysiology of Involuntary Movements in Parkinson's Disease, Yanagisawa, et al., Euro. Neurol, vol. 26, Suppl 1., © 1987 S. Karger A.G., pp. 30-40.
The Unified Parkinson's Disease Rating Scale (UPDRS): Status and Recommendations, Movement Disorder Society Task Force on Rating Scales for Parkinson's Disease, Goetz et al., Movement Disorders, vol. 18, No. 7, 2003, pp. 738-750.
The accuracy and precision of timing of self-paced, repetitive movements in subjects with Parkinson's disease, O'Boyle, et al., Brain 1996, vol. 119, © 1996 Oxford University Press pp. 51-70.
Nov. 15, 2017—(EP) Extended Search Report—App. 12758333.7.
Dunnewold, R.J. W et al., "Quantitative Assessment of Bradykinesia in Patients with Parkinson's Disease", Journal of Neuroscience Methods, Elsevier Science Publisher B.V., Jun. 6, 1997, vol. 74, No. 1, pp. 107-112.
Evans, Andrew H. et al., "A Conditioned Response as a Measure of Impulsive-Compulsive Behaviours in Parkinson's Disease", PLoS One, vol. 9, No. 2, Feb. 24, 2014, p. e89319, XP055300236, doi:10.1371/journal.bone.0089319.
Griffiths, Robert I., "Automated Assessment of Bradykinesia and Dyskinesia in Parkinson's Disease", Journal of Parkinson's Disease, vol. 2, No. 1, Jan. 1, 2012, pp. 47-55, XP055300735, doi: 10.3233/JPD-2012-11071.
Patel, Shyamal et al., "Monitoring Motor Fluctuations in Patients with Parkinson's Disease using Wearable Sensors", IEEE Transactions on Information Technology in Biomedicine, Nov. 1, 2009, vol. 13, No. 6, pp. 864-873.
Patel, Shyamal et al., "Using Wearable Sensors to Enhance DBS Parameter Adjustment for Parkinson's Disease Patients through Measures of Motor Response", Proceedings of the 3rd IEEE-EMBS International Summer School and Symposium on Medical Devices and Biosensors, Sep. 1, 2006, pp. 141-144, ISBN: 978-0-7803-9786-6.
Patel, Shyamal, "Using Wearable Sensors to Predict the Severity of Symptoms and Motor Complications in late stage Parkinson's Disease", 30th Annual International IEEE EMBS Conference, Engineering in Medicine and Biology Society, Aug. 20, 2008, Piscataway, NJ, pp. 3686-3689.
Veltink, P. H. et al., "Towards a New Method for Kinematic Quantification of Bradykinesia in Pateints with Parkinson's Disease using Triaxial Accelerometry", IEEE 17th Annual Conference montreal, Quebec, Canada, Engineering in Medician and Biology Society, Sep. 20, 1995, pp. 21303-21304, ISBN: 978-0-7803-2475-6.
Zwartjes, Daphne G.M. et al., "Ambulatory Monitoring of Activities and Motor Symptoms in Parkinson's Disease", IEEE Transactions on Biomedical Engineering, vol. 57, No. 11, IEEE Service Center, Piscataway, NJ, Nov. 1, 2010, pp. 2778-2786, XP011327061, ISSN: 0018-9294, doi: 10.1109/TBME.2010.2049573.

\* cited by examiner

METHOD AND SYSTEM FOR ASSESSING MOTION SYMPTOMS

CROSS-REFERENCE TO RELATED APPLICATIONS

This application claims the benefit of Australian Provisional Patent Application No. 2014900683 filed 3 Mar. 2014, and the benefit of Australian Provisional Patent Application No. 2014903705 filed 17 Sep. 2014, each of which is incorporated herein by reference.

TECHNICAL FIELD

The present invention relates to determining and/or monitoring a state of progression in an individual of a disease or treatment having motion symptoms, by analysing the kinetic state of the individual, and in particular the invention relates to a method and system for monitoring bradykinesia and/or dyskinesia to assess the state of progression of the disease or treatment.

BACKGROUND OF THE INVENTION

A range of diseases, medications, trauma and other factors can lead to a person having motion symptoms. Motion symptoms include dyskinesia, in which the person is in a hyperkinetic state, and bradykinesia, in which the person is in a hypokinetic state.

For example, bradykinesia is a key manifestation of Parkinson's disease (PD). L-Dopa, or Levodopa, is often administered to patients having Parkinson's disease, and can have the effect of causing the patient to become dyskinetic for a period of time after administration. However, even for new patients the half-life of levodopa is only of the order about 90 minutes. As Parkinson's disease progresses, the half life of L-Dopa shortens and the effective dose range decreases, making dosage control extremely difficult and complex. This is commonly managed by increasing the dose frequency, sometimes to as many as ten doses each day in an attempt to control symptoms and enable the patient to have a reasonable quality of life. Thus, patients with Parkinson's disease may experience periods of bradykinesia, dyskinesia and normal motor function several times a day and throughout the course of a single dose of L-Dopa.

Even if a satisfactory dosage regime is reached at one point in time, the progressive nature of Parkinson's disease means that neurologists must regularly review a patient's symptoms in order to effectively control the patient's ongoing treatment dosage. Without objective and ongoing monitoring it is very difficult for physicians to avoid prescribing either an excessive dose which overly increases episodes of dyskinesia, or an inadequate dose which does not prevent episodes of bradykinesia. Furthermore conventional clinical treatment relies on a subjective assessment undertaken by a physician, and gives no objective measure to indicate whether a change in dose was effective in improving symptoms.

Further, clinical observation typically only occurs over a short period of patient attendance, usually of the order of tens of minutes, once every 6 or 8 weeks. Fluctuations in kinetic state throughout the day and from one day to the next significantly complicate attempts at assessing the patient's kinetic state. Clinicians often rely on the patient's recollection and/or written diaries to gain an understanding of the ongoing kinetic state of the patient between clinical appointments. However patients can rarely give objective scores, and the effect of a kinetic episode itself can often make it difficult for a patient to make any record whatsoever of the nature of and timing of motor fluctuations.

Monitoring the course of Parkinson's in an individual, and determining when more advanced therapies might become appropriate, requires considerable clinical expertise over an extended period. Advanced therapies for treating symptoms of Parkinson's disease include deep brain stimulation (DBS), Amantadine, Apomorphine by continuous infusion, and levodopa-carbidopa intestinal gel. However, it remains a problem to detect the stage at which conventional therapies such as levodopa are no longer controlling symptoms, and at which more advanced therapies are needed. For some patients, particularly the elderly, the window of time in which to adopt some advanced therapies can be relatively short as DBS can be ineffective if commenced too late, so that failure to promptly recognise the need for advanced therapies can result in the patient entirely missing out on the opportunity to adopt and benefit from such therapies.

In the case of DBS for example, it has been shown that DBS is an effective treatment of PD, for well-selected PD patients. That is, an accurate patient selection is crucial to ensure positive outcomes. Patient selection for DBS usually happens at two stages. First, in clinic, a general neurologist selects the patient as a potential DBS candidate and refers him/her to a DBS surgical centre. Second, at the DBS surgical centre, a team of DBS specialists, including a movement disorders neurologist with expertise in selection and management of DBS patients, determines whether a DBS therapy is recommended for the patient. However, general neurologists who are not expert in movement disorders have difficulty in deciding when to refer patients for consideration for DBS surgery. Indeed studies have shown that the first stage of patient selection suffers from unsatisfactory referral accuracy and that, depending for example on the referring clinician, up to 60% or even 80% of the patients referred are refused by DBS surgical centres. This imposes an unnecessary burden on both the DBS surgical centres, and the patients and their caregivers who undergo unnecessary visits and tests. At the same time, under-referral in the first stage may also exist, which withholds appropriate DBS candidates from the opportunity of being assessed in the second stage and gaining a benefit from DBS therapy.

Moreover, the second stage of DBS patient selection noted above typically involves a comprehensive selection process, including levodopa challenge assessment, brain Magnetic Resonance Imaging (MRI) and evaluation of neuropsychological and psychiatric functions.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of determining a state of progression in an individual of a disease or treatment having motion symptoms, the method comprising;

obtaining a time series of accelerometer data from an accelerometer worn on an extremity of the person, over an extended period during everyday activities of the person;

processing the accelerometer data to produce a plurality of measures of kinetic state of the individual at a respective plurality of times throughout the extended period, each measure of kinetic state comprising at least one of: a measure for bradykinesia, and a measure for dyskinesia;

determining a measure of dispersion of the measures of kinetic state; and generating an output indicating that motion symptoms are at an initial stage if the measure of dispersion is less than a threshold, and generating an output indicating that motion symptoms are at an advanced stage if the measure of dispersion is greater than the threshold.

According to a second aspect, the present invention provides a non-transitory computer readable medium for determining a state of progression in an individual of a disease or treatment having motion symptoms, comprising instructions which, when executed by one or more processors, causes performance of the following:

obtaining a time series of accelerometer data from an accelerometer worn on an extremity of the person, over an extended period during everyday activities of the person;

processing the accelerometer data to produce a plurality of measures of kinetic state of the individual at a respective plurality of times throughout the extended period, each measure of kinetic state comprising at least one of: a measure for bradykinesia, and a measure for dyskinesia;

determining a measure of dispersion of the measures of kinetic state; and generating an output indicating that motion symptoms are at an initial stage if the measure of dispersion is less than a threshold, and generating an output indicating that motion symptoms are at an advanced stage if the measure of dispersion is greater than the threshold.

The measure of dispersion could in some embodiments be a measure of the numerical distance between a high and low percentile of the measures of kinetic state, and for example may be a measure of the interquartile range of the measures of kinetic state. Alternatively, the measure of dispersion could be a measure of the variance of the measures of kinetic state. Alternatively, the measure of dispersion could be a measure of the standard deviation of the measures of kinetic state, or other indicator of the variability, scatter, or spread of the measures of kinetic state.

The extended period may comprise more than one day and for example may comprise 10 days. During the extended period, the accelerometer data is preferably obtained for the present method only during waking hours, for example during the period between 9:00 AM and 6:00 PM for each of the days during the extended period, or during an adaptive awake period defined by an automatic measure of somnolence.

The present invention recognises that, in Parkinson's disease for example, an increase in an individual's fluctuation between ON, OFF and dyskinetic states is a predictor of the individual needing advanced therapies. Thus, monitoring for elevation of a measure of dispersion of kinetic state measurements beyond a threshold provides for an automated method for monitoring progression of the disease and medication response.

In some embodiments, each measure of kinetic state comprises both a measure for bradykinesia and a measure for dyskinesia. In such embodiments, the measure of dispersion may be produced as a weighted sum of a measure of the dispersion of the measures for bradykinesia and a measure of the dispersion of the measures for dyskinesia. The weights may each be 0.5, or any other weight in the range of −1 to 1, inclusive. In alternative embodiments, the measure of dispersion may be produced by summing each measure of bradykinesia with a contemporaneous measure of dyskinesia to produce a combined measure of kinetic state, and determining the measure of dispersion from the dispersion of the combined measures of kinetic state.

In some embodiments, the measure of dispersion may be produced by first processing the measure of the dispersion of the measures for bradykinesia and/or the measure of the dispersion of the measures for dyskinesia using a mathematical function or respective mathematical functions. The processed measures in some embodiments may then be summed linearly to produce the measure of dispersion. The or each mathematical function may comprise applying a weighting as discussed above and/or may comprise applying a logarithmic or exponential to the respective measures, for example.

In some embodiments the method of the present invention may simply determine whether the measure of dispersion exceeds the threshold, to give a binary output. However, alternative embodiments may further comprise recording the value of the measure of dispersion as determined on different occasions in order to monitor progression of the measure of dispersion, for example over the course of weeks, months or years. Some embodiments may additionally or alternatively monitor a rate of change in the measure of dispersion over time, for example to project or predict disease progression towards a threshold at which advanced therapies may become appropriate. Moreover, monitoring the measure of dispersion during progression of a disease may in some embodiments be used as a basis to indicate which therapy, of a plurality of available progressions in therapy, is suitable for that particular patient.

The threshold against which the measure of dispersion is compared in order to determine whether the individual might require advanced therapy may be determined or predefined in any suitable manner. For example, the threshold may be predefined as being the median value of the measure of dispersion for normal subjects, or the median level of the measure of dispersion for subjects having received advanced therapy, or the 75th percentile level of the measure of dispersion for subjects having received advanced therapy, or a scalar, logarithmic or exponential variant derived from such values, or the like. In embodiments in which the measure of kinetic state is normalised to a scale of 0-100, and in which the measure of dispersion comprises the interquartile range, a suitable value for the threshold may be in the range 25-40. In other embodiments, the measure of dispersion may be derived from scores of bradykinesia alone, for example when assessing PD onset or early stage PD at which time bradykinesia dominates, in which case the threshold of interquartile range may be in the range 15 to 25. In other embodiments the measure of dispersion may be derived from scores of dyskinesia alone, for example when assessing late stage PD or advanced therapy eligibility at times when dyskinesia dominates, in which case a suitable threshold for interquartile range may be in the range 3-20, more preferably 5-10. The threshold may be defined relative to a standard deviation of a population when the measure of dispersion is based solely or largely on scores of bradykinesia, noting that bradykinesia scores are substantially normally distributed unlike dyskinesia scores.

The dyskinesia scores may in some embodiments be produced in accordance with the teachings of International Patent Application Publication No. WO 2009/149520, the content of which is incorporated herein by reference. The bradykinesia scores may in some embodiments be produced in accordance with the teachings of WO 2009/149520.

The output, indicating that motion symptoms are either at an initial stage or at an advanced stage, in preferred embodiments is communicated to a physician in order that the physician may consider whether to prescribe or administer an altered or advanced therapy. For example, the output may be provided to a general neurologist undertaking a first stage of DBS patient selection, and/or to a DBS specialist undertaking a second stage of DBS patient selection. Such embodiments may thus provide a quantitative, simple, automatic, and accurate patient screening tool to support general neurologists in the referral stage, and/or DBS specialists in the DBS eligibility assessment of the individual.

The measure of dispersion may additionally or alternatively be used to guide refinements to dosages, whether dosages of medicaments, or dosages or characteristics of DBS stimuli for a DBS recipient. An advanced stage of motion symptoms identified by the present invention may thus indicate a need for revised dosage, mix or selection of oral medications, such as an advance from levodopa to a levodopa-carbidopa mix, and/or may indicate a need for advanced therapies such as deep brain stimulation (DBS), Amantadine, Apomorphine by continuous infusion, drug delivery by a patch, and levodopa-carbidopa intestinal gel delivered by pump, and/or may indicate any other suitable progression or change in therapy.

In some embodiments, the method may further comprise aggregating measures of dispersion obtained for a plurality of individuals in order to assess a state or progression of disease or treatment of the group. Such embodiments may for example be utilised to assess a geographical region or jurisdiction, a clinic, a clinician, or a class of patients, for example to assess whether a country, a region, a clinic or an individual clinician is over- or under-treating their patients, or is prescribing advanced therapies at an appropriate time as compared to other countries, regions, clinics or clinicians.

BRIEF DESCRIPTION OF THE DRAWINGS

An example of the invention will now be described with reference to the accompanying drawings, in which.

DESCRIPTION OF THE PREFERRED EMBODIMENTS

Figure 1:
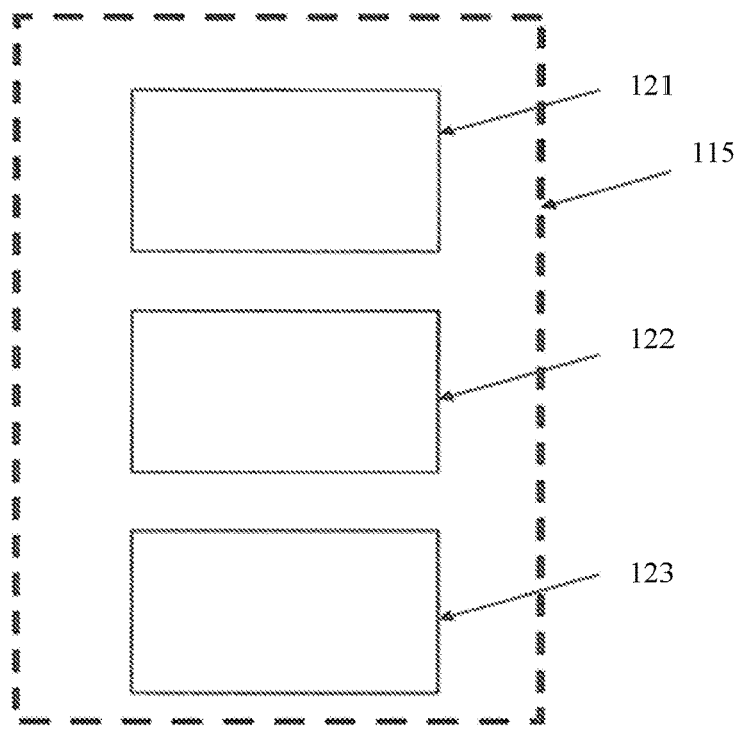
FIG. 1 is a diagrammatic view of a means for detection of various Parkinsonian clinical states in accordance with an embodiment of the invention.

FIG. 1 is a diagrammatic view of a device for detection of various Parkinsonian or kinetic states in accordance with an embodiment of the invention. The device is wrist mounted which provides a sufficiently accurate representation of the kinetic state of the whole body. The device 115 comprises three elements for obtaining movement data of a limb of a person. The device 115 comprises a motion monitor 121 in the form of an accelerometer, an assessor 122 for recording and analysis of the received data in a manner that provides an objective determination of bradykinesia and dyskinesia, and an output means 123 for outputting objective determination of bradykinesia or dyskinesia over time periods so as to allow a clinician to prescribe medications or to allow the person to better understand their own kinetic state.

The device 115 is a light weight device which is intended to be worn on the most affected wrist of the person throughout waking hours. The device is mounted on an elastic wrist band so as to be firmly supported enough that it does not wobble on the arm and therefore does not exaggerate accelerations. The device is configured to rise away from the person's wrist by a minimal amount so as to minimise exaggeration of movements.

The accelerometer 121 records acceleration in three axes X, Y, Z over the bandwidth 0-10 Hz, and stores the three channels of data in memory on-board the device. This device has 1 GB of storage so as to allow data to be stored on the device for up to 10 days, after which the data can be downloaded and analysed.

Figure 2:
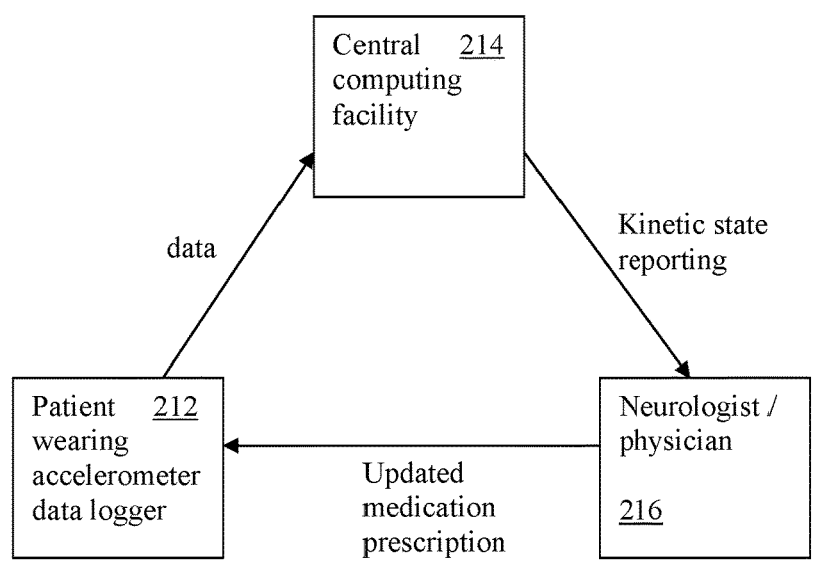
FIG. 2 illustrates kinetic state monitoring and reporting in accordance with one embodiment of the invention.

FIG. 2 illustrates kinetic state monitoring and reporting in accordance with one embodiment of the invention. A patient 212 is wearing the device of FIG. 1. The device 115 logs accelerometer data and communicates it to a central computing facility 214. The computing facility 214 analyses the data to produce an output indicating whether motion symptoms are at an initial stage or an advanced stage. The output is reported to a neurologist 216, either by email or by being made available on a website on the Internet, in a format which can be rapidly interpreted by the neurologist to ensure efficient use of the neurologist's time. The neurologist 216 then interprets the report and optimises the patient's medication or therapy accordingly.

In this embodiment algorithms are applied to the obtained data by a central computing facility 214 in order to generate both a dyskinesia score and a bradykinesia score for every 2 minute window of data, in the manner taught by WO 2009/149520.

Figure 3:
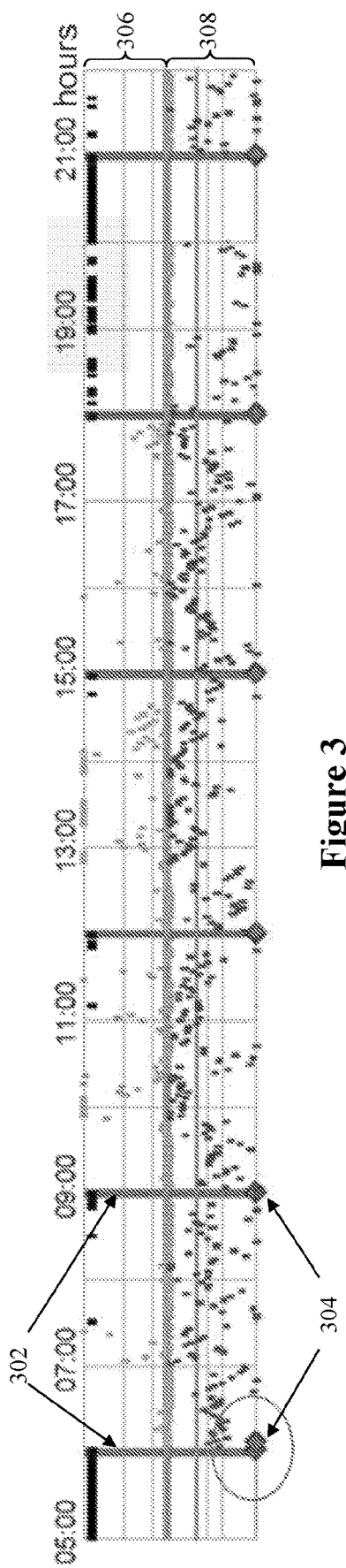
FIG. 3 gives an example of the output from one day of wrist-worn data logger recording from a patient.

FIG. 3 gives an example of the output from one day of wrist-worn data logger recording from a patient who was prescribed 6 doses of levodopa per day. The upper set of data points 306 represent the dyskinesia scores (DK scores) produced from each 2 minute window of data, and the lower set of data points 308 represent the bradykinesia scores (BK scores) produced from each 2 minute window of data. DK scores are plotted only on or above the midline of FIG. 3, while BK scores are plotted only on or below the midline of FIG. 3. Greater severity of dyskinesia is represented by increasing distance of the DK scores 306 upwards from the midline, while greater severity of bradykinesia is represented by increasing distance of the BK scores 308 downwards from the midline. The horizontal lines indicate the respective median, 75th percentile and 90th percentile of controls, for both DK and BK scores. The six vertical lines, of which two are indicated at 302, indicate the times at which medications were prescribed, and the diamonds 304 represent when the taking of medication was acknowledged by the patient.

The present embodiment recognises that dispersion, or greater fluctuations, in the DK scores 306 and/or BK scores 308 over an extended period, is a useful predictor of whether motion symptoms have progressed to an advanced stage.

A study was conducted in which patients wore the device of FIG. 1 for 10 days, and all data was collected. A fluctuation score, in accordance with one embodiment of the invention, was determined from the data as follows:

a) the interquartile range of all DK scores 306 was determined from the 10 days data set;

b) the interquartile range of all BK scores 308 was determined from the 10 days data set;

c) the results of steps (a) and (b) were summed together to produce the fluctuation score.

The interquartile range for both the DK and BK scores is defined as the difference between (a) the value below which 75% of all data points fall and (b) the value below which 25% of all data points fall.

Figure 4:
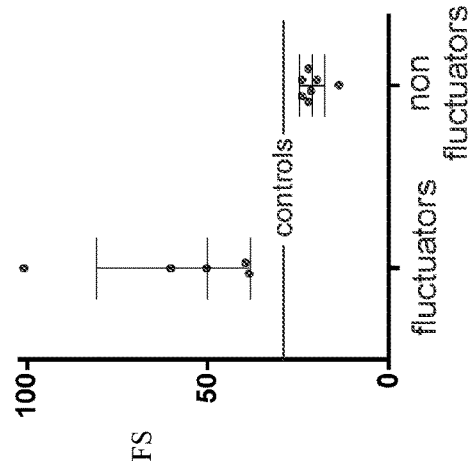
FIG. 4 illustrates the measure of dispersion, or fluctuation score, for patients at an initial disease state, and at an advanced disease state, respectively.

The median BK scores correlate with contemporaneously obtained clinical ratings using the Unified Parkinson's rating Scale part III (UPDRS3), and the median DK scores correlate with clinically obtained ratings using the modified Abnormal Involuntary Movement Score (AIMS) rating. The fluctuation score was tested in a group of people with Parkinson's who were categorised by a neurologist as either being fluctuators (at an initial disease state) or non fluctuators (at an advanced disease state), as reflected in FIG. 4. As can be seen in FIG. 4, the scores from the fluctuation score were completely separate in fluctuators and non fluctuators revealing that the fluctuation score proved suitably sensitive to fluctuations in the BK and DK scores and is thus a good predictor of disease state.

Figure 5:
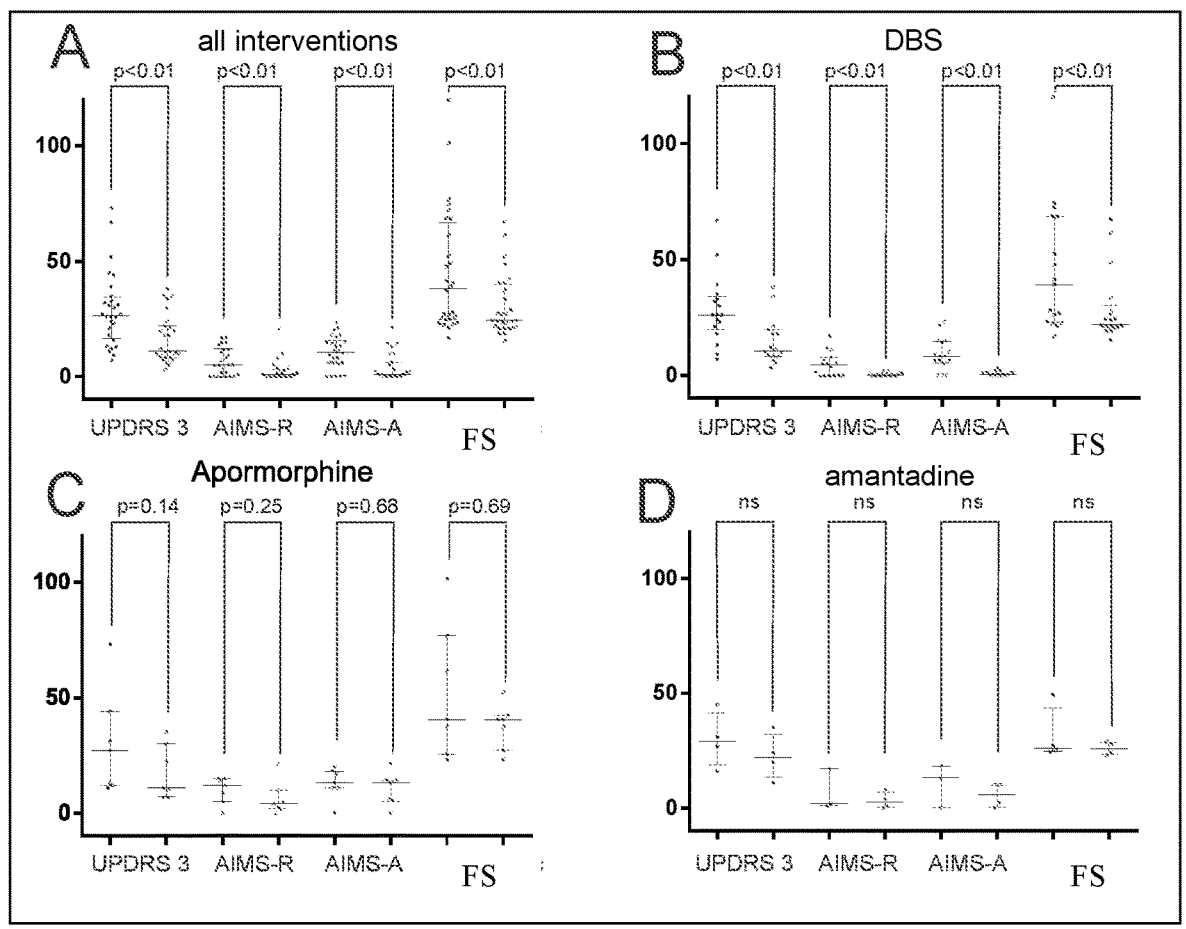
FIG. 5 illustrates utility of the fluctuation score in relation to patients already having received advanced interventions.

This fluctuation score was then further examined in relation to patients already having received advanced interventions, including DBS, Amantadine and Apomorphine (FIG. 5A) and compared with UPDRS 3, AIMS resting (AIMS-R) and AIMS active (AIMS-A). Each of these measures demonstrated significant benefit from the interventions (p<0.01 Mann Whitney). Next the change in scores following each of the interventions were measured separately: only DBS produced a significant change and the extent of the change was similar and of equal significance by each measure (See Table 1).

TABLE 1

Statistics for DBS See FIG. 2B

|  | UPDRS 3 | | AIMS-R | | AIMS-A | | Fluctuation score | |
| --- | --- | --- | --- | --- | --- | --- | --- | --- |
|  | before | after | before | after | before | After | before | after |
| Median | 26 | 10.5 | 4.5 | 0 | 8 | 0.5 | 38.9 | 21.7 |
| IQR | 14.5 | 11.5 | 7.75 | 1 | 9.5 | 1 | 45.85 | 9.55 |

The fluctuation score thus detects changes produced by advanced therapies.

Figure 6:
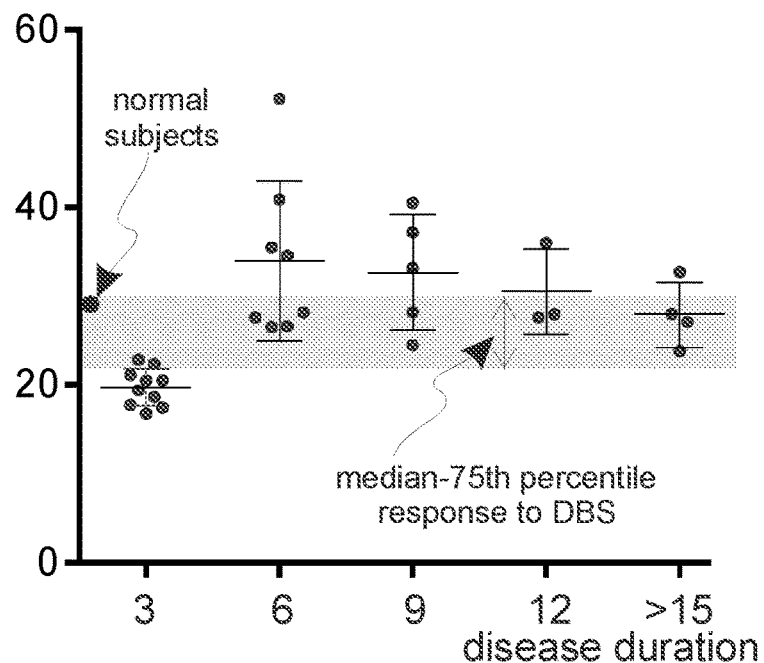
FIG. 6 illustrates how the fluctuation score changes over the course of disease.

To investigate how the fluctuation score changes over the course of progression of disease, the fluctuation score was assessed in 30 people with Parkinson's with various durations since diagnosis (FIG. 6). In FIG. 6 the subjects have had the disease for varying durations, but none had advanced therapies. The lower level of the shaded grey band represents the median value of the fluctuation score following DBS, and the upper level of the grey band is the 75th percentile of the fluctuation score metric following DBS. Note the median of normal subjects was also plotted (black circle in FIG. 6). First it is apparent that people with early PD have a low (compared to normal) fluctuation score and that this rises toward normal in subjects who have longer disease duration. In a proportion of subjects the levels rise well above the level of controls. This occurs early in disease (between 3-6 years) and at a time when fluctuations would be expected to commence. Such patients, who exceed the $50^{th}$ and/or $75^{th}$ percentile of DBS recipients, may thus be likely to benefit from receiving a deep brain stimulator and therefore may be candidates for advanced therapy.

Figure 7:
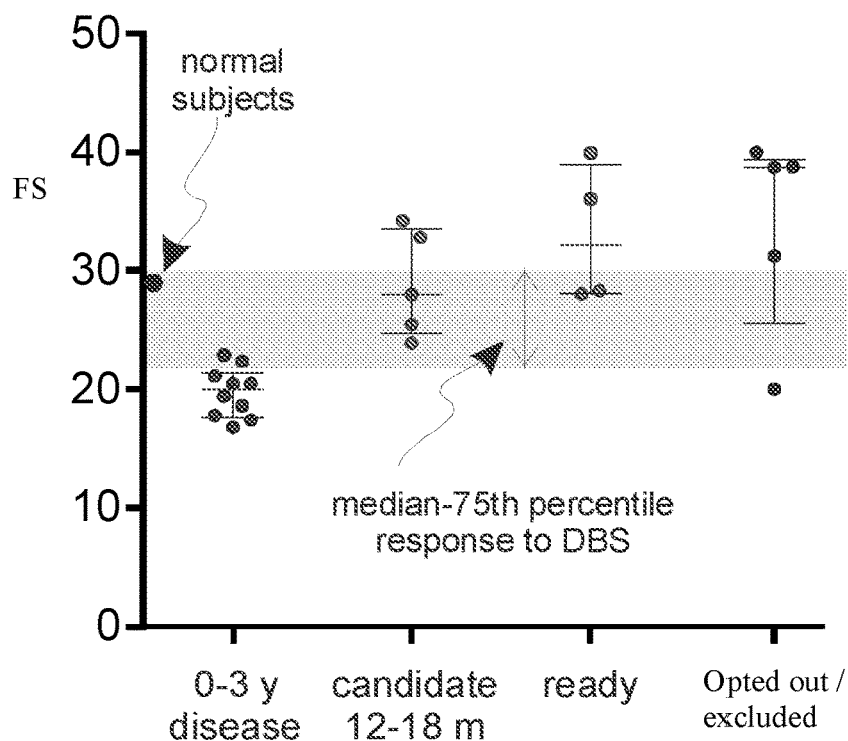
FIG. 7 illustrates how the fluctuation score changes over the course of disease.

To investigate how the fluctuation score changes in relation to candidates for advanced therapy, consulting neurologists were asked to classify patients into three categories: i) those who are likely to be candidates for advanced therapies in the next 12-18 months, ii) those who are now candidates for advanced therapy but have not yet commenced treatment, and iii) subjects who should/could have advanced therapy on motor grounds but who have chosen against it or are excluded by other non-motor grounds. Also, subjects who had PD for 0-3 years as plotted in FIG. 6 are also included in FIG. 7 for comparison. FIG. 7 suggests that the rise in the fluctuation score is in keeping with a rise toward suitability for advanced therapy.

In FIG. 7 the lower level of the shaded grey band represents the median fluctuation score following DBS and the upper level is the 75th percentile of the fluctuation score following DBS. Note the median of normal subjects is at a similar level as the $75^{th}$ percentile for post-DBS subjects.

Thus the fluctuation score could be used to identify candidates for advanced therapies. When the fluctuation score of a PD patient increases from the low values typical of the "0-3 year" cohort and enters the region between the median and 75th percentile "response" to DBS it may be an indication that the patient is or soon will be a candidate for advanced therapies (see FIG. 7).

Figure 8A:
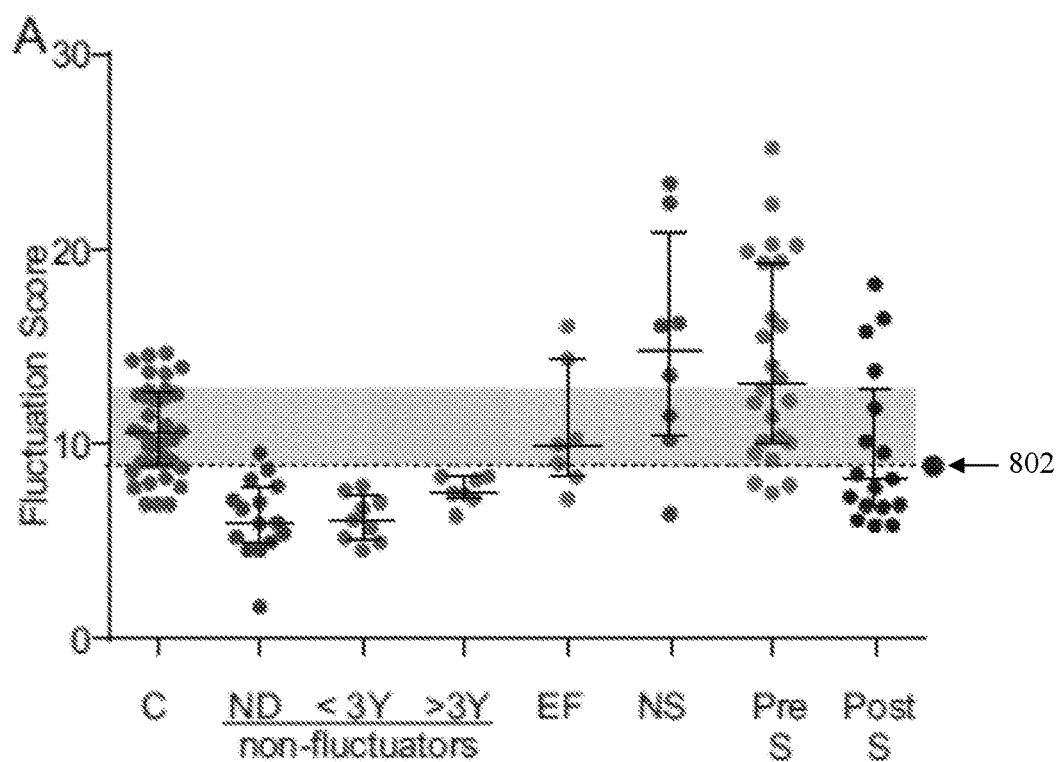
FIGS. 8a and 8b illustrate the fluctuation score (FS) of subjects at various stages of PD.

The ability of the fluctuation score to map the transition of a patient from non-fluctuator to fluctuator was examined in further detail. In this further study the fluctuation score was determined as above, and is referred to as a fluctuation score (FS). The FS of subjects at various stages of PD was compared, as shown in FIG. 8a. In particular, FIG. 8a shows the FS of the following groups: (i) 38 subjects without PD aged between 45 and 85, being control subjects (C); (ii)

people with PD who were newly Diagnosed (ND), (iii) people with PD who had had the disease less than 3 years and were non fluctuators (<3Y); (iv) people with PD who had had the disease more than 3 years and were non fluctuators (>3Y), (v) people with PD who were Early Fluctuators (EF), (vi) people with PD who were Fluctuators but Not Suitable (NS) for DBS, (vii) people with PD who were on the waiting list Pre Surgery (Pre-S), and (viii) people with PD who were post-surgery recipients of DBS (post S). Some of these subjects are shown in previous figures. The dotted line with a black circle indicated at 802 is the FS that separates fluctuators and non-fluctuators and is referred to as the fluctuation threshold (FT, at FS=7.7). The grey shaded region is the region between the FS for the median and 75$^{th}$ percentile of Post DBS subjects (FS=12.8), referred to herein as the range for control of motor symptoms (RCMS). It is noted that this region coincides with the interquartile range of controls C.

FIG. 8a enables the FS of the ND, <3Y, >3Y, EF, NS, Pre S and Post S cohorts to be compared. There is a trend for the FS to progressively increase from early disease (<3Y) to late disease (>3Y), even though the FS remained below the fluctuation threshold 802. The FS of early fluctuators (EF) had moved above the FT but for most EF patients the FS was still within the RCMS. The median FS of the NS and Pre S cohorts was above the 75$^{th}$ percentile of the post-surgery group. The difference in FS between controls (C) and newly diagnosed PD (ND) was significant (p<0.0001, Mann Whitney).

Figure 8B:
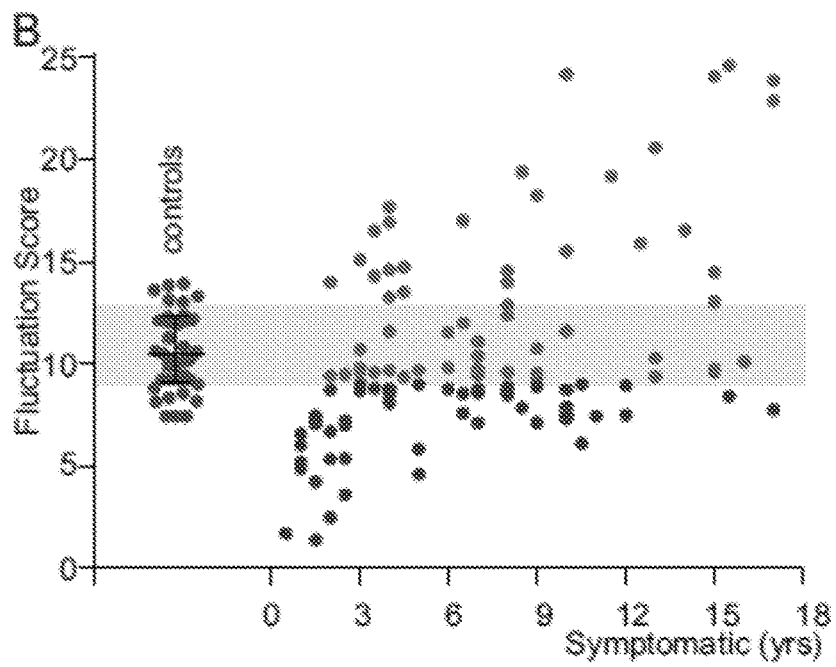

This was further examined in 177 subjects (FIG. 8b), selected retrospectively from all subjects who had worn the body worn data collection device for more than 6 days, whose time from symptom onset was known and who had also been assessed using AIMS. FIG. 8b shows the FS of 177 subjects plotted against duration since first symptoms. A FS within or above the RCMS became frequent after 3 years. The FS of Control subjects (from FIG. 4A) is included. Some subjects who had disease for many years had FS below the median of controls, and some patients' FS was even below the FT after many years of disease, suggesting that some may have been poorly responsive to dopaminergic stimulation. Note that this is a population attending a movement disorder clinic and not a controlled population sample, and may thus be biased toward those with a greater tendency toward fluctuating disease and younger patients. This cohort was then subdivided according to their AIMS (table 2).

TABLE 2

| | AIMS | | | | |
|---|---|---|---|---|---|
| | >2 | 2-5 | 6-9 | 2-9 | >10 |
| No. of subjects | 96 | 25 | 16 | 41 | 34 |
| 25% Percentile of FS | 6.8 | 8.8 | 8.1 | 8.5 | 12.2 |
| Median of FS | 8.0 | 9.8 | 9.4 | 9.7 | 14.6 |
| 75% Percentile of FS | 9.7 | 14.7 | 12.6 | 14.3 | 20.3 |
| | | P = 0.6 | | <0.0001 | |
| Mann Whitney | | P < 0.005 | | | |

The median FS of those cases with an AIMS of 1 or 0 was 8.0 and 65% of FS were below the FT: most likely the higher FS were due to variation in the bradykinesia score. There was no statistical difference in the FS's of subjects with AIMS between 2-5 and 6-9 so these were pooled (see "2-9" column) and were statistically different to those with higher (>10) or lower AIMS. Broadly, subjects with AIMS of 2 or less, between 2-9 and greater than 10 approximated the FS below the FT, within the RCMS and above the RCMS (respectively).

Figure 9A:
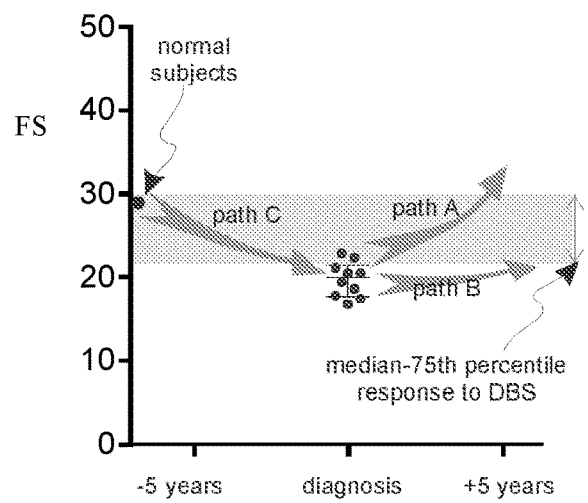
FIGS. 9a and 9b illustrate likely pathways of how the fluctuation score may change over the course of disease.
Figure 9B:
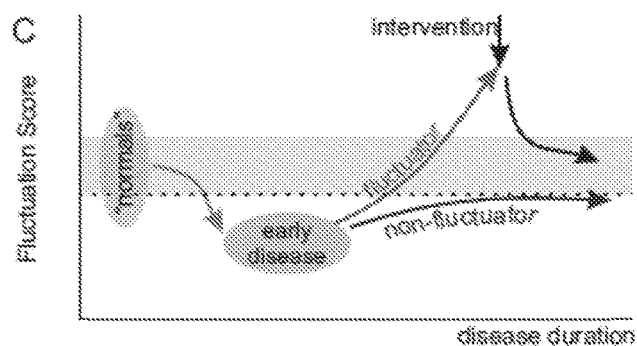

Without intending to be limited by theory, it is to be anticipated that subjects in their first years of disease will reveal two broad pathways: one consistent with fluctuations (path A in FIG. 9a) and one consistent with non fluctuators and a poorer response (path B in FIG. 9a). In more detail, the range in FS of control subjects and the effect of therapy on the FS in early PD raises questions around whether the transition from non-fluctuator to fluctuator should be defined by a single score (the FT) or a range (such as the bottom half of the RCMS). FIG. 9b similarly depicts the possible changes in FS over the course of PD, and is based on inspection of FIGS. 8a and 8b above. The shaded horizontal band represents the range in FS produced by an intervention such as DBS with the upper limit being the upper level of an acceptable response and the lower limit being the FT (shown by the dotted line in FIG. 9b). It is proposed that as normal subjects have an FS in this band and newly diagnosed PD patients have a FS below the FT, PD must initially produce a steady decline in FS until a diagnosis is made. With treatment and time, some subjects will have a progressive increase in their FS, eventually crossing the cross-over point and finally becoming a frank fluctuator and suitable for an intervention. We predict that some subjects who have a poor response to dopaminergic stimulation or cannot be aggressively treated will maintain a low FS and may even progressively decline (indicated in FIG. 9b as "non-fluctuators"). FIG. 9b suggests that patients will either persist with a FS in or just below the lower half of the RCMS for many years of disease, or else will transition to having FS scores well above the RCMS. This data is drawn from a specialist clinic and may under represent the patients with low FS who are unresponsive to levodopa. Clearly an early detection of those subjects who are on the "fluctuator" pathway of FIG. 9b would lead to timely and effective intervention with DBS.

In summary, we propose that an FS derived from the variation in the BKS and DKS of a movement symptoms data series has the potential to be used as a tool for choosing and optimising therapies for patients with PD.

The combination of a falling fluctuation score and asymmetry between the fluctuation score in the left and right side (by equipping the patient with a suitable accelerometer data gathering device on each wrist) will detect people with early motor symptoms.

Figure 10A:
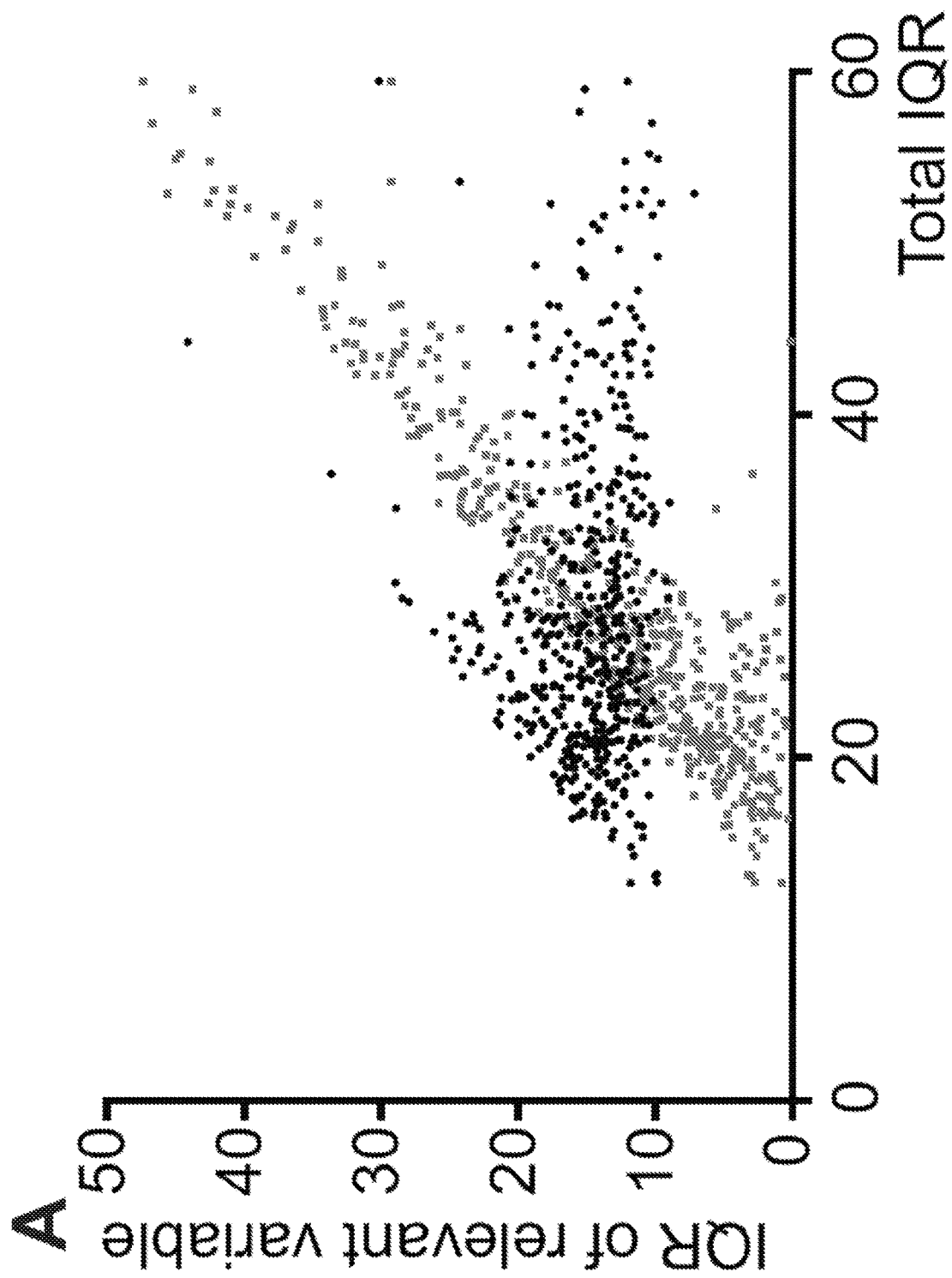
FIGS. 10a and 10b illustrate the respective contribution of the BK score and the DK score to the FS.
Figure 10B:
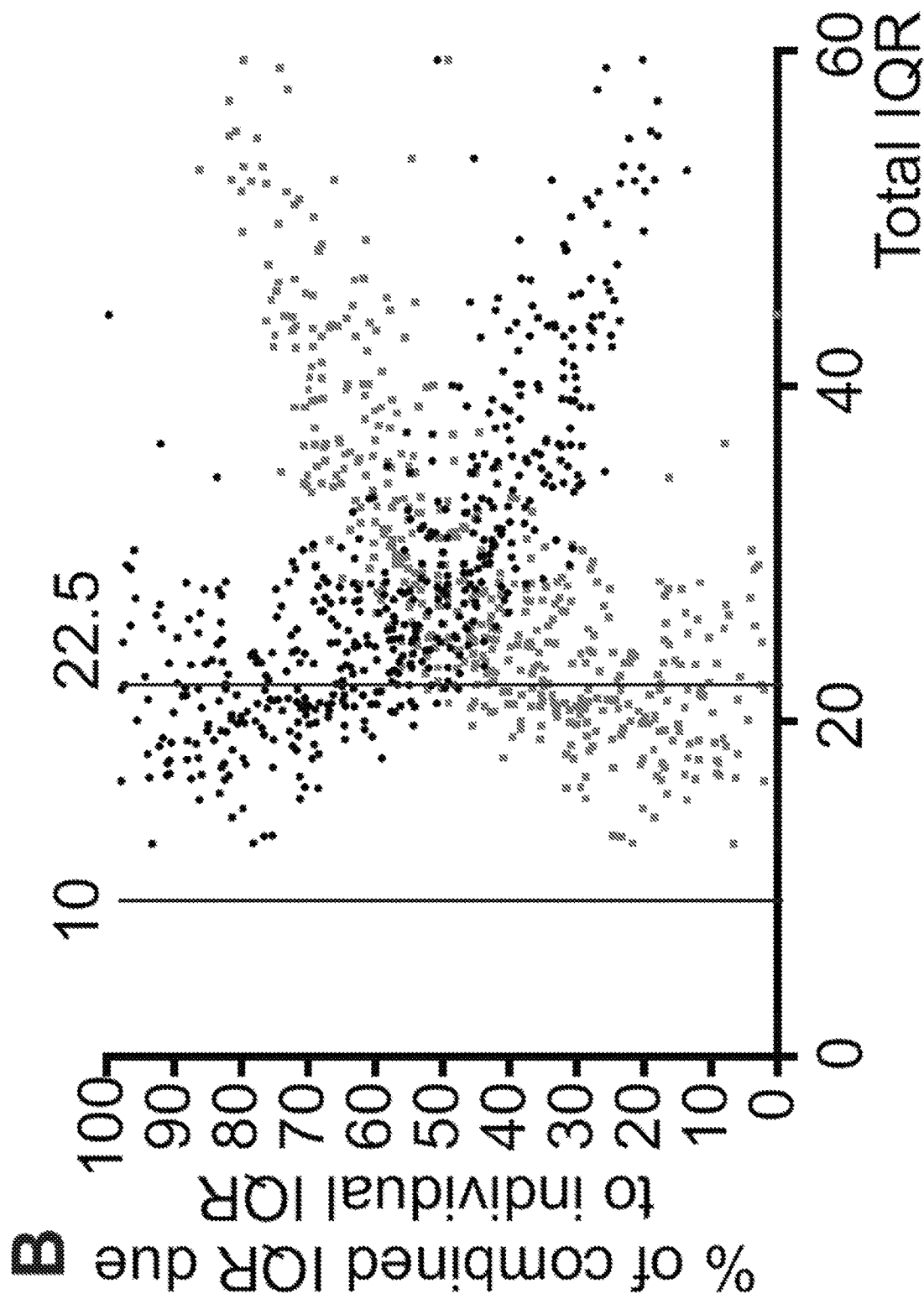

It is thus proposed that the size of the Interquartile Range (IQR) of the BKS and DKS provided by the presently proposed fluctuation score or FS reflects the extent of fluctuations. To further investigate this proposition, the IQR of the BKS and DKS ($BKS_{IQR}$ and $DKS_{IQR}$) were extracted from 527 patients' recordings and the combined IQR ($IQR_C$) for each patient was calculated. The $BKS_{IQR}$ and $DKS_{IQR}$ for each patient was plotted against the $IQR_C$ (FIG. 10a). This shows that the $BKS_{IQR}$ is greater than the $DKS_{IQR}$ when the $IQR_C$ is <~25. This is more readily apparent when the $BKS_{IQR}$ and $DKS_{IQR}$ for each patient was expressed as a percentage of the $IQR_C$ and plotted against the $IQR_C$ (FIG. 10b). Note that there no $IQR_C$ values which are less than 10. As the IQRs are measures of variation in the score, it implies that the $DKS_{IQR}$ dominates when $IQR_C$ is large, whereas variability of the BKS (the $BKS_{IQR}$) is more significant when $IQR_C$ is lower. Note the vertical line at an $IQR_C$=22.5, where the $BKS_{IQR}$ contributes about 60% to the $IQR_C$, corresponds to the point that separates fluctuators and non fluctuators in FIG. 2, showing that both $BKS_{IQR}$ and $DKS_{IQR}$ contribute significantly to the $IQR_C$ at this point.

We therefore addressed the question of whether one or both of the $BKS_{IQR}$ and $DKS_{IQR}$ were required to detect fluctuations.

Figure 11A:
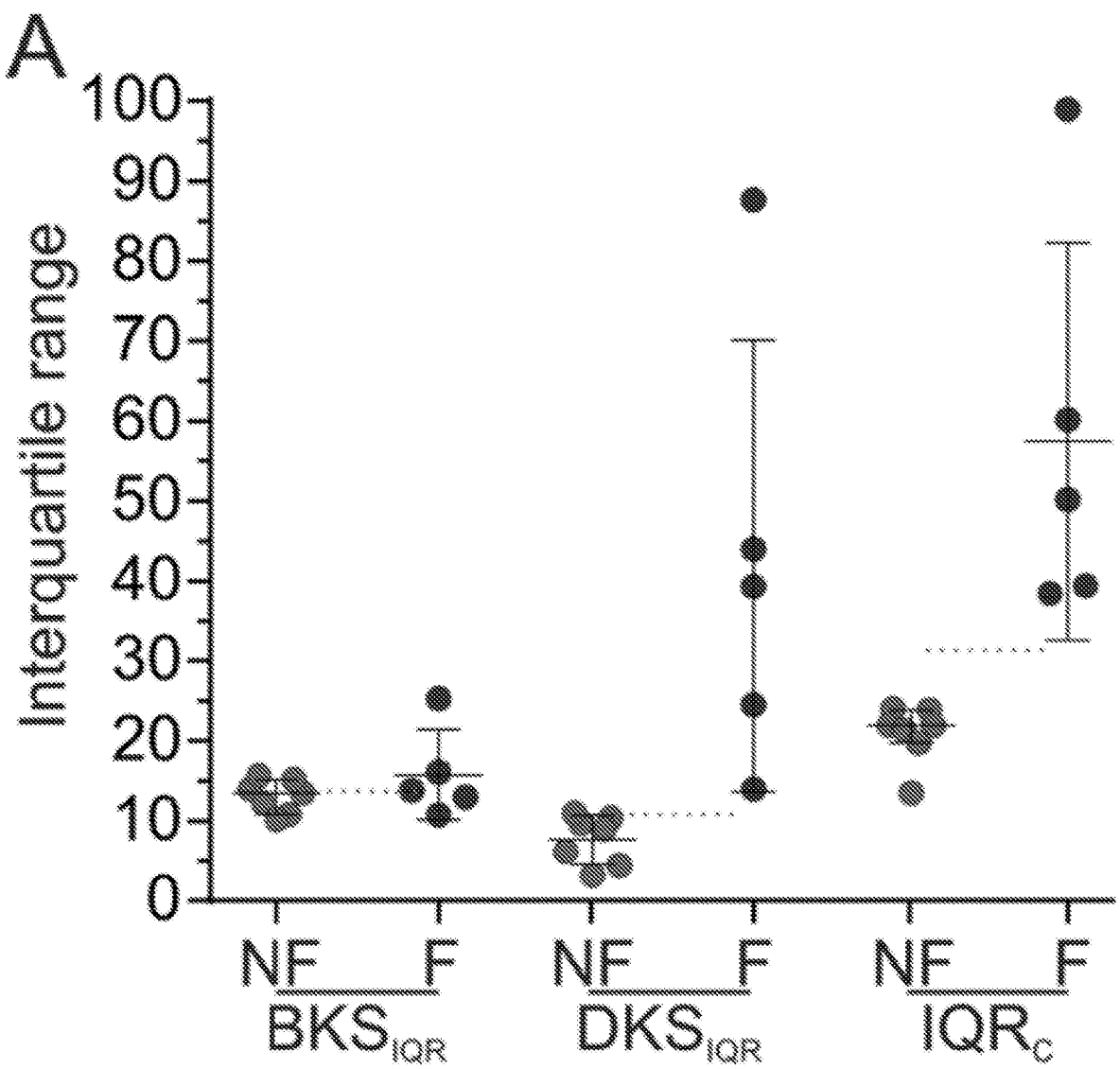
FIGS. 11a, 11b, and 11c illustrate the improved selectivity of the FS as compared to the BK or DK scores alone.

The validity of these IQR measures was first tested against a small sample of subjects with (n=5) and without (n=7) fluctuations. Their classification was blinded while the IQR measurements were applied (FIG. 11a). In FIG. 11a the $BKS_{IQR}$, $DKS_{IQR}$ and $IQR_C$ of fluctuators (F) and non fluctuating (NF) patients were plotted. While the two populations are separated into two distinct IQR scores using either $DKS_{IQR}$ and $IQR_C$, the separation is more distinct populations using the $IQR_C$. The dotted line corresponds to an $IQR_C$ of 31.4. While the $DKS_{IQR}$ provided separation, the $IQR_C$ provided greater separation although both had an area under the ROC of 1.0. The validity of the $IQR_C$ was further tested by comparing it against a second group of fluctuators (n=36) who were on the waiting list for insertion of deep brain stimulators (DBS) and a group of non fluctuators (n=16), who all had PD for three years or less (FIG. 11b).

Figure 11B:
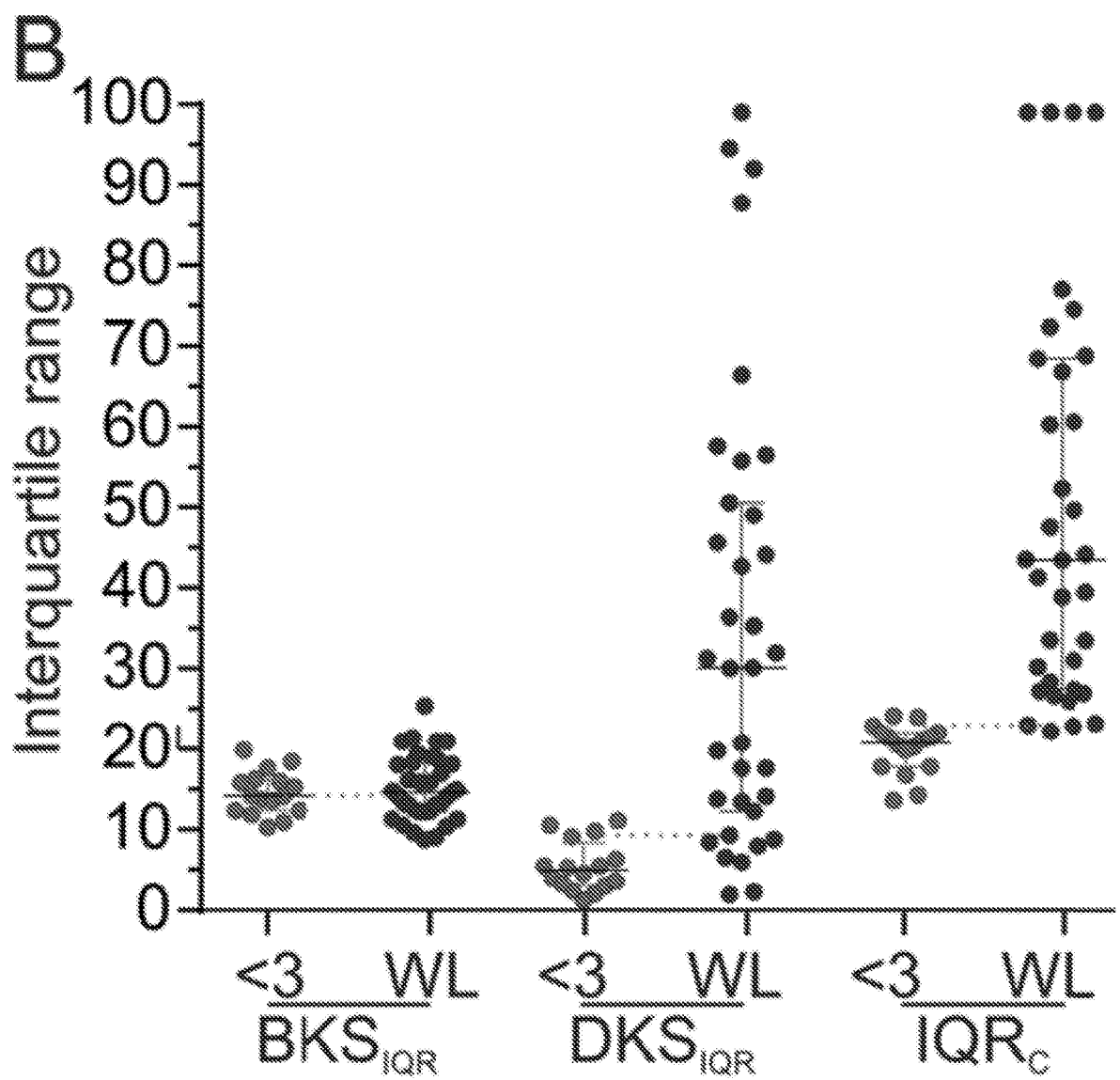

FIG. 11b is a plot of the $BKS_{IQR}$, $DKS_{IQR}$ and $IQR_C$ of patients with PD for less than 3 years (<3) and of patients on the waiting list for DBS (WL). The dotted line corresponds to an $IQR_C$ of 22.5 which separates the two groups with greater sensitivity and selectivity than the $DKS_{IQR}$. Note that all $IQR_C$>100 have been shown as =100. Error bars show median and interquartile range. The median modified AIMS when active for those on the waiting list was 7 (range 1-23) and there was no dyskinesia (measured by AIMS) in the non fluctuators. The median $IQR_C$ of the non fluctuators was 20.8 (IQR: 17.8-22.1) and 43.4.0 (IQR: 27.4-68.5) for those on the waiting list. There was a significant difference between these two populations (p<0.0001. Mann Whitney). The area under the receiver Operator Curve for $IQR_C$ was 0.98 and provided a Sensitivity of 97.1% and Selectivity of 87.5% at an $IQR_C$ of 22.5. In comparison, the Sensitivity and Selectivity of the $DKS_{IQR}$ was 80% and 81% and examination of FIG. 11b shows the degree of overlap. Thus, both contributions in the variation in the BKS and DKS are required to establish a cut-off point between fluctuators and non fluctuators. It is of interest that in FIG. 10, the cut-off point between fluctuators and non fluctuators (the line marked by 22.5) is at a point where the $BKS_{IQR}$ contributes more than 50% of the $IQR_C$. Thus while the variability in the DKS is the main contributor to discriminating between fluctuators and non fluctuators, at the cut-off point variation in the BKS and DKS both contribute.

Figure 11C:
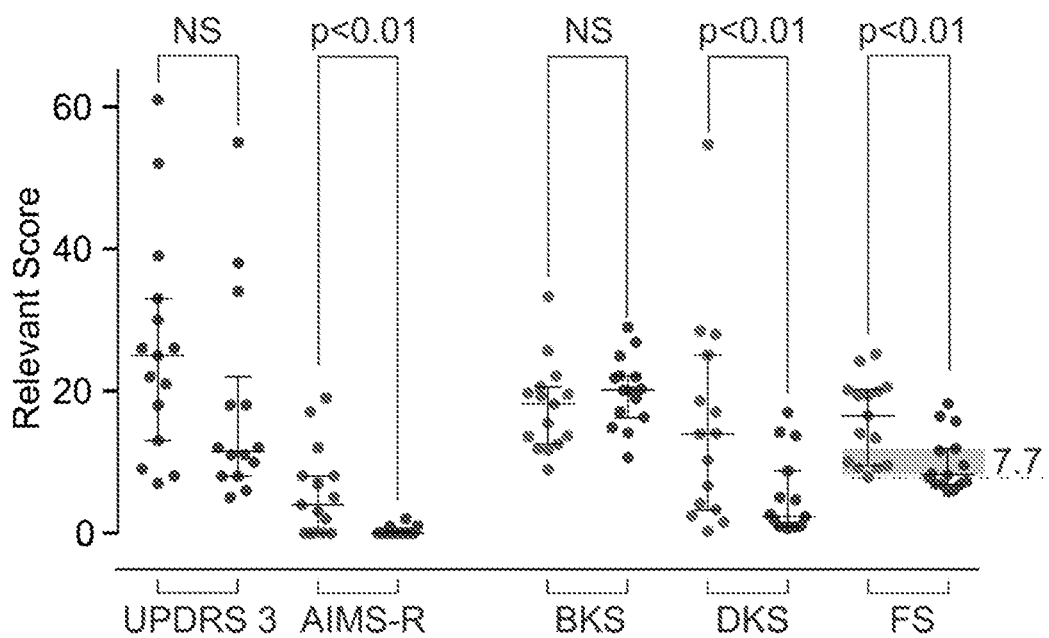

FIG. 11c further illustrates the benefit of the FS as compared to $BKS_{IQR}$ or $DKS_{IQR}$. This shows the median and interquartile range of rating scores (UPDRS 3, and AIMS-R) as well as the $BKS_{IQR}$, $DKS_{IQR}$ and FS measures, before and after DBS in 15 PD patients. The Y axis is the relevant value of the respective scale or measure. The FS threshold for transition from non fluctuators to fluctuators (see FIG. 9b) is indicated by a dotted line. The shaded region is the area between the median and $75^{th}$ percentile of the FS (being the range 8.2 to 12.8) after DBS. Note that the median FS after DBS (8.2) is very close to the value that separates fluctuators from non fluctuators in FIG. 8a (FS=7.7) In FIG. 11c error bars show median and interquartile range. P values are obtained using Mann Whitney.

Although the $IQR_C$ does appear to distinguish fluctuators from non fluctuators, the weighting given to each of the $BKS_{IQR}$ and $DKS_{IQR}$ was investigated. Thus a general formula was introduced:

Fluctuation Score=$s \times BKS_{IQR} + t \times DKS_{IQR}$ where $s$ and $t$ were independent weightings applied to $BKS_{IQR}$ and $DKS_{IQR}$.

A family of Fluctuation Scores (FS) were produced by independently and serially varying s and t from 0.1 to 5.0. Each FS was used to produce a p value by comparing the early PD and those on the DBS waiting list (in FIG. 11b). The p values varied from 0.6 to <0 0001, with the lowest being provided by a weighting of 1.0 for both s and t: i.e. the original $I_{QRC}$ is appropriate.

Inspection of FIG. 10 shows that the $IQR_C$ is never less than 10 and that the $IQR_C$ can become very large (the x axis was clipped at 100 with data points >100 shown at that point). Thus the $IQR_C$ was expressed as a log with the offset of 10 removed to improve the visual effect in a plot. Thus FS=$\log^{1.1}(IQR_C)-25$ (note that 25 is ~Log(10.8)).

Figure 12A:
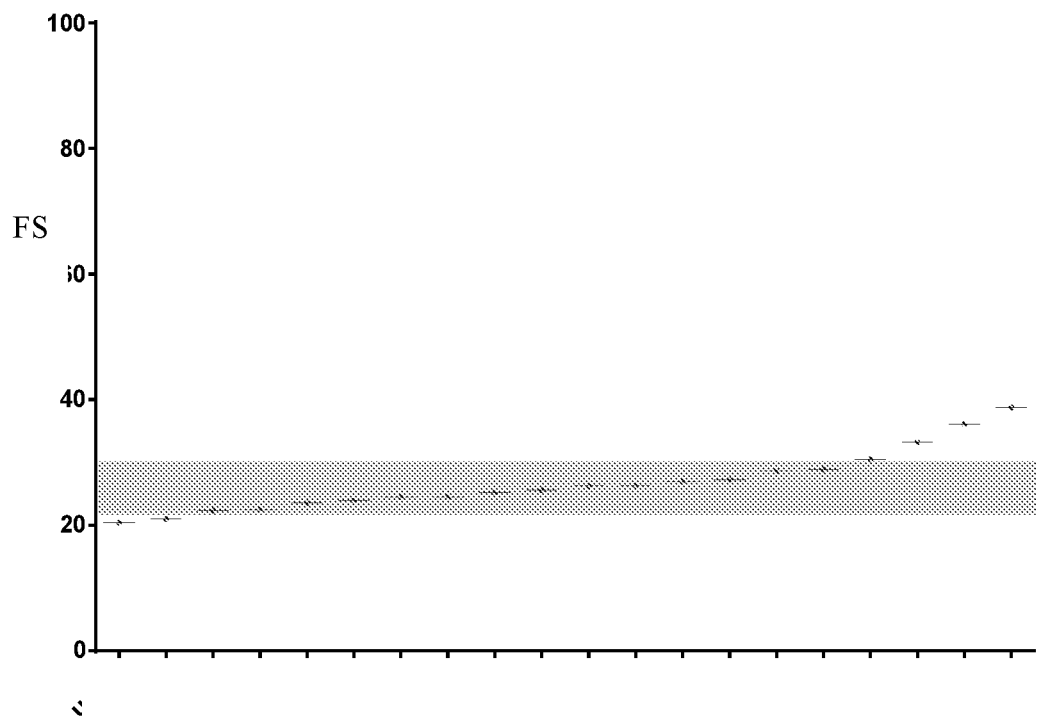
FIG. 12 illustrates an examination of patient populations using the fluctuation score to find DBS candidates.
Figure 12B:
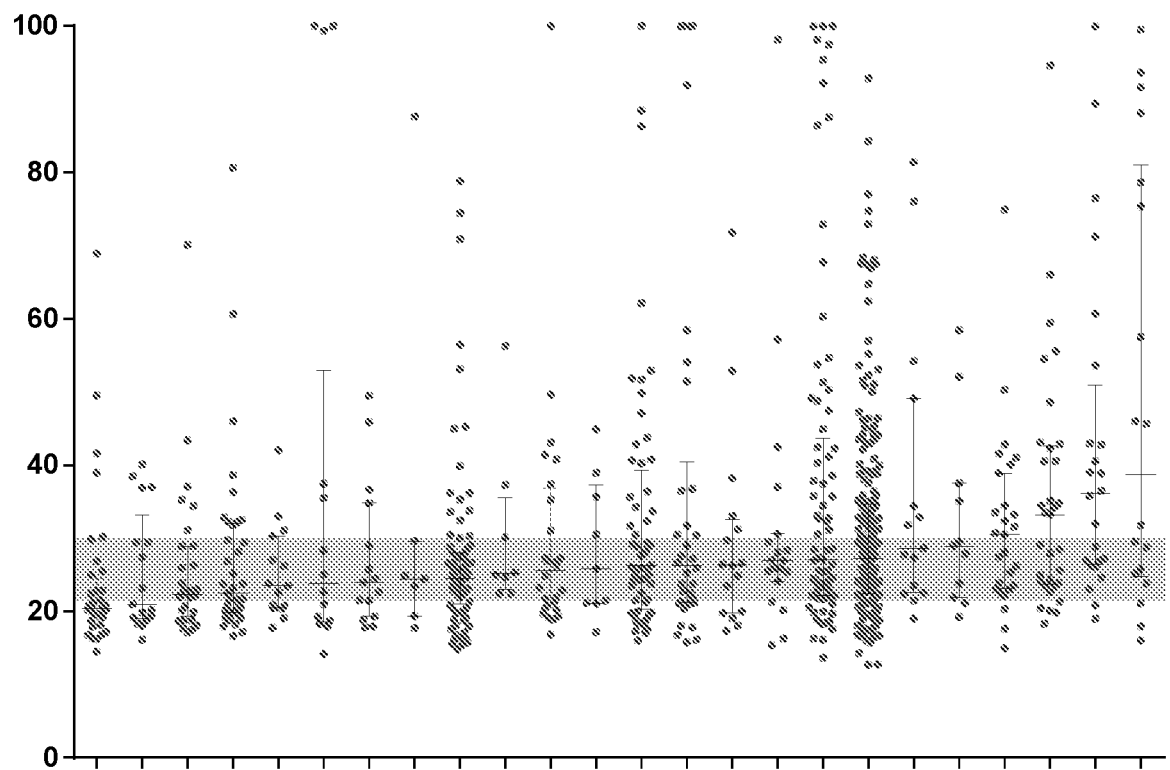

FIG. 12 illustrates an examination of patient populations using the fluctuation score to find DBS candidates. In both FIGS. 12a and 12b, the Y axis is the Fluctuation Score and the X axis groups patients by clinic for selected clinics in Australia. In each clinic's population, the lines in FIG. 12a show the median value for that clinic. In FIG. 12b, the median, interquartile range, and individual subjects' FS are shown. In both FIGS. 12a and 12b, the bottom edge of the horizontal shaded band is the FT, being the point that discriminates between fluctuators (below) and non fluctuators (above). The top of the shaded band is the $75^{th}$ percentile of the response to DBS. Above this point a person would be a clear candidate for DBS or other advanced therapy. Accordingly, it is possible to use the FS to examine a population of clinics and direct such advanced therapies more appropriately.

It is to be appreciated that patients may be grouped by clinic as shown in FIG. 12 or may be grouped by any other factor such as clinician, region or country. For example where it is determined that a region or country is under-treating their patient group the present invention provides a means to direct additional resources where appropriate.

Some portions of this detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

As such, it will be understood that such acts and operations, which are at times referred to as being computer-executed, include the manipulation by the processing unit of the computer of electrical signals representing data in a structured form. This manipulation transforms the data or maintains it at locations in the memory system of the computer, which reconfigures or otherwise alters the operation of the computer in a manner well understood by those skilled in the art. The data structures where data is maintained are physical locations of the memory that have particular properties defined by the format of the data. However, while the invention is described in the foregoing context, it is not meant to be limiting as those of skill in the art will appreciate that various of the acts and operations described may also be implemented in hardware.

It should be borne in mind, however, that all of these and similar terms are to be associated with the appropriate physical quantities and are merely convenient labels applied to these quantities. Unless specifically stated otherwise as apparent from the description, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Figure 13:
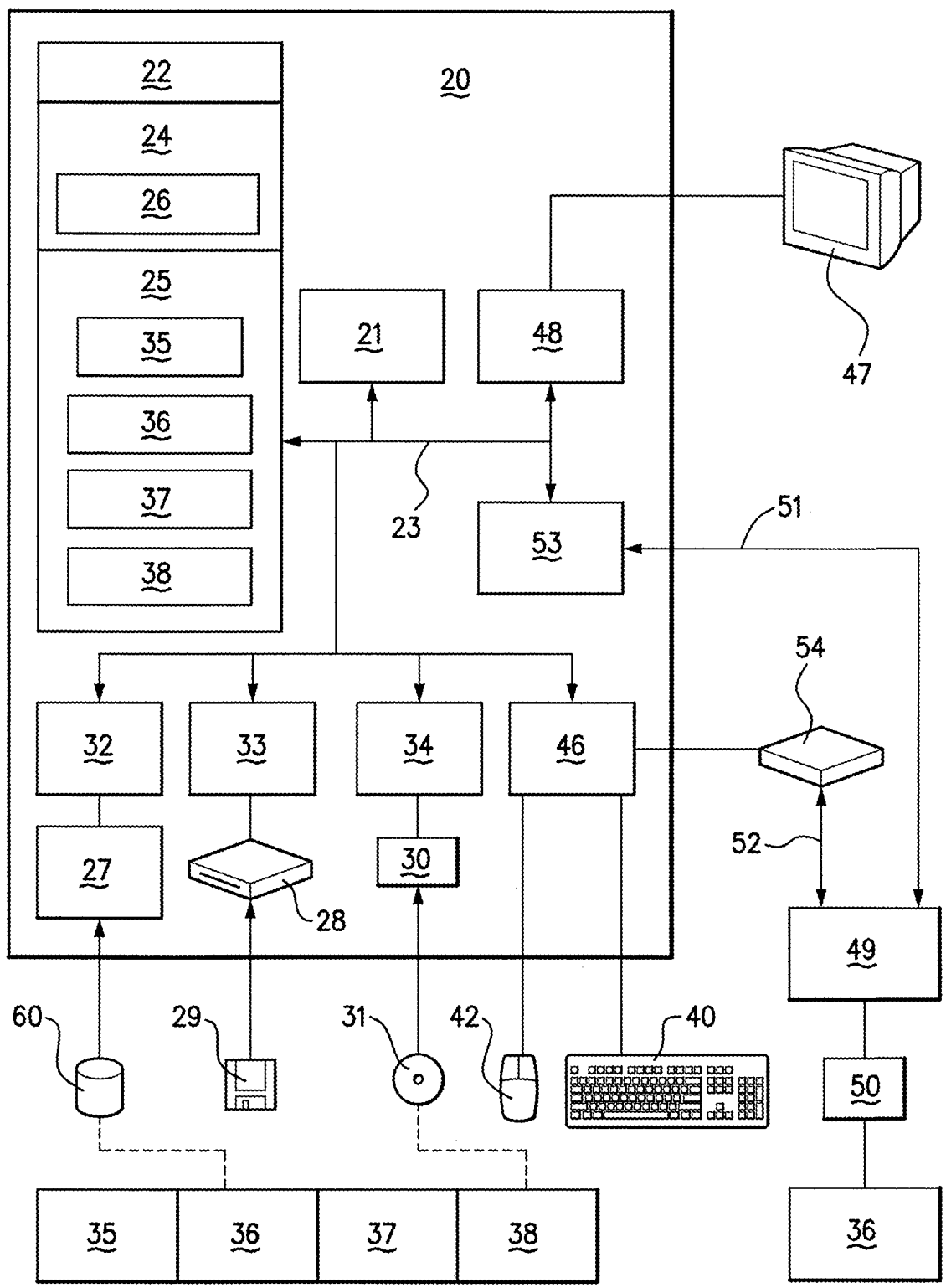
FIG. 13 illustrates a general-purpose computing device that may be used in an exemplary system for implementing the invention.

Turning to FIG. 13, the invention is illustrated as being implemented in a suitable computing environment. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multi-processor systems, microprocessor-based or programmable consumer electronics, network PCs, minicomputers, mainframe computers, and the like. The invention may be practiced in distributed computing environments where tasks are performed by remote processing devices that are linked through a communications network. In a distributed computing environment, program modules may be located in both local and remote memory storage devices.

In FIG. 13 a general purpose computing device is shown in the form of a conventional personal computer 20, including a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help to transfer information between elements within the personal computer 20, such as during start-up, is stored in ROM 24. The personal computer 20 further includes a hard disk drive 27 for reading from and writing to a hard disk 60, a magnetic disk drive 28 for reading from or writing to a removable magnetic disk 29, and an optical disk drive 30 for reading from or writing to a removable optical disk 31 such as a CD ROM or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer readable instructions, data structures, program modules and other data for the personal computer 20. Although the exemplary environment shown employs a hard disk 60, a removable magnetic disk 29, and a removable optical disk 31, it will be appreciated by those skilled in the art that other types of computer readable media which can store data that is accessible by a computer, such as magnetic cassettes, flash memory cards, digital video disks, Bernoulli cartridges, random access memories, read only memories, storage area networks, and the like may also be used in the exemplary operating environment.

A number of program modules may be stored on the hard disk 60, magnetic disk 29, optical disk 31, ROM 24 or RAM 25, including an operating system 35, one or more applications programs 36, other program modules 37, and program data 38. A user may enter commands and information into the personal computer 20 through input devices such as a keyboard 40 and a pointing device 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB) or a network interface card. A monitor 47 or other type of display device is also connected to the system bus 23 via an interface, such as a video adapter 48. In addition to the monitor, personal computers typically include other peripheral output devices, not shown, such as speakers and printers.

The personal computer 20 may operate in a networked environment using logical connections to one or more remote computers, such as a remote computer 49. The remote computer 49 may be another personal computer, a server, a router, a network PC, a peer device or other common network node, and typically includes many or all of the elements described above relative to the personal computer 20, although only a memory storage device 50 has been illustrated. The logical connections depicted include a local area network (LAN) 51 and a wide area network (WAN) 52. Such networking environments are commonplace in offices, enterprise-wide computer networks, intranets and, inter alia, the Internet.

When used in a LAN networking environment, the personal computer 20 is connected to local network 51 through network interface or adapter 53. When used in a WAN networking environment, the personal computer 20 typically includes modem 54 or other means for establishing communications over WAN 52. The modem 54, which may be internal or external, is connected to system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of determining a state of progression in an individual with Parkinson's disease, the method comprising:
   receiving a time series of accelerometer data obtained from an accelerometer of a wrist-mounted device worn on a wrist of the individual over an extended period of time during everyday activities of the individual;
   determining, by a processor and based on the time series of accelerometer data, a plurality of measures of kinetic state of the individual at a plurality of times throughout the extended period of time, each measure of kinetic state comprising a measure for bradykinesia and a measure for dyskinesia;
   determining, by the processor, a measure of dispersion of the measures of kinetic state including a measure of dispersion of the measure for bradykinesia and a measure of dispersion of the measure for dyskinesia;
   calculating, by the processor, a Fluctuation Score using a function including a weighted sum of the measure of dispersion of the measure for bradykinesia and the measure of dispersion of the measure for dyskinesia;
   responsive to the Fluctuation Score being less than a threshold, displaying, by a display device, a first output indicating that Parkinson's disease is at an initial stage to assess treatment thereof; and
   responsive to the Fluctuation Score being greater than the threshold, displaying, by the display device, a second output indicating that Parkinson's disease is at an advanced stage to assess treatment thereof.

2. The method of claim 1, wherein the measure of dispersion comprises a measure of an interquartile range of the measures of kinetic state.

3. The method of claim 1, wherein the measure of dispersion comprises a measure of a standard deviation of the measures of kinetic state.

4. The method of claim 1, wherein the measure of dispersion comprises a measure of a variance of the measures of kinetic state.

5. The method of claim 1, wherein the extended period of time comprises more than one day.

6. The of claim 5, wherein the extended period of time comprises 10 days.

7. The method of claim 1, wherein during the extended period of time, the accelerometer data is obtained only when the individual is awake.

8. The method of claim 1, wherein the weights are equal.

9. The method of claim 1, wherein the measure of dispersion is determined by summing each measure of bradykinesia with a contemporaneous measure of dyskinesia to produce a combined measure of kinetic state, and the Fluctuation Score is determined from the dispersion of the combined measures of kinetic state.

10. The method of claim 1, wherein the method is used to obtain Fluctuation Scores for a plurality of individuals, and further comprising aggregating a plurality of measures of dispersion in order to assess a state or progression of Parkinson's disease or treatment therefor, for the group of individuals.

* * * * *